United States Patent
Horiba et al.

(10) Patent No.: US 7,812,172 B2
(45) Date of Patent: Oct. 12, 2010

(54) THIAZOLOTHIAZOLE DERIVATIVE

(75) Inventors: Koji Horiba, Kanagawa (JP); Hidekazu Hirose, Kanagawa (JP); Akira Imai, Kanagawa (JP); Katsuhiro Sato, Kanagawa (JP); Takeshi Agata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 0 days.

(21) Appl. No.: 12/430,361

(22) Filed: Apr. 27, 2009

(65) Prior Publication Data

US 2010/0137611 A1 Jun. 3, 2010

(30) Foreign Application Priority Data

Dec. 2, 2008 (JP) .............................. 2008-307217
Mar. 19, 2009 (JP) .............................. 2009-067966

(51) Int. Cl.
 *C07D 513/04* (2006.01)
(52) U.S. Cl. ...................................................... 548/153
(58) Field of Classification Search .................. 548/153
 See application file for complete search history.

(56) References Cited

U.S. PATENT DOCUMENTS 3,250,617 A 5/1966 Sawdey

FOREIGN PATENT DOCUMENTS

JP   A-2006-206503   8/2006
JP   A-2007-126403   5/2007

OTHER PUBLICATIONS

Sato et at., "Application of Organic EL Device to Flat Panel Display," *Technical Report of IEICE. OME 95-54, The Institute of Electronics, Information and Communication Engineers*, pp. 47-52, 1995 (with Partial Translation).

Ando et al., "Synthesis, physical properties, and field-effect transistors of novel thiophene/thiazolothizole co-oligomers," *Journal of Materials Chemistry*, vol. 14, pp. 1787-1790, 2004.

Ando et al., "Characterization and Field-Effect Transistor Performance of Heterocyclic Oligomers Containing a Thiazolothiazole Unit," *Chemistry Letters*, vol. 33, No. 9, pp. 1170-1171, 2004.

Johnson et al., "Thiazolothiazoles. II. Parent Heterocycle and its carboxylic and amino derivatives," *Journal of the American Chemical Society*, vol. 92, No. 13, pp. 4046-4050, Jul. 1, 1970.

Ando, et al., "High Performance n-Type Organic Field-Effect Transistors Based on π-Electronic Systems with Trifluoromethylphenyl Groups," Journal of the American Chemical Society, vol. 127, pp. 5336-5337, 2005, XP-002534244.

Ando, et al., "Synthesis, Physical Properties and Field-Effect Transistors of Novel Thiazolothiazole-Phenylene Co-Oligomers," Journal of Materials Chemistry, vol. 17, No. 6, pp. 553-558, 2007, XP-002534304 (Abstract Only).

*Primary Examiner*—Kamal A Saeed
*Assistant Examiner*—Nyeemah Grazier
(74) *Attorney, Agent, or Firm*—Oliff & Berridge, PLC

(57) ABSTRACT

A thiazolothiazole derivative is represented by the following Formula (I). In Formula (I), each $R^1$ independently represents a straight chain alkyl group having 3 to 20 carbon atoms, a straight chain alkoxy group having 3 to 20 carbon atoms, a branched alkyl group having 3 to 20 carbon atoms, or a branched alkoxy group having 3 to 20 carbon atoms; and each $R^2$ independently represents a hydrogen atom, a straight chain alkyl group having 1 to 20 carbon atoms, a straight chain alkoxy group having 1 to 20 carbon atoms, a branched alkyl group having 3 to 20 carbon atoms, or a branched alkoxy group having 3 to 20 carbon atoms.

(I)

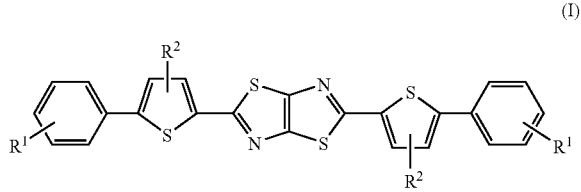

6 Claims, 20 Drawing Sheets

THIAZOLOTHIAZOLE DERIVATIVE

CROSS-REFERENCE TO RELATED APPLICATIONS

This application is based on and claims priority under 35 USC 119 from Japanese Patent Applications No. 2008-307217 filed on Dec. 2, 2008 and No. 2009-067966 filed on Mar. 19, 2009.

BACKGROUND

1. Technical Field

The present invention relates to a thiazolothiazole derivative.

2. Related Art

Charge transport materials are important materials in organic electronic devices such as organic photoreceptors, organic electroluminescence devices, organic transistors, and organic optical memories, because efficient reception of generated charges and quick transfer of the charges lead to improved performance and life-time of the organic electronic devices.

Therefore, the charge transport materials have been developed focusing on the properties such as charge mobility and charge injection property, from the viewpoint of improving the performance thereof.

Known examples of thiazolothiazole derivatives include thiazolothiazole derivatives represented by Formulae 2 to 4 shown below, which are described in S. Ando, J. Nishida, et al., *J. Mater. Chem.*, vol. 14, pp. 1787-1790 (2004) and S. Ando, J. Nishida, et al. *Chemistry Letters*, vol. 33, No. 9, pp. 1170-1171 (2004); films of the thiazolothiazole derivatives represented by Formula 3 and 4 are formed by a vapor-deposition method.

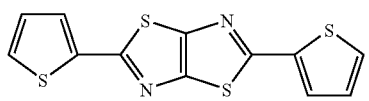

Formula 2

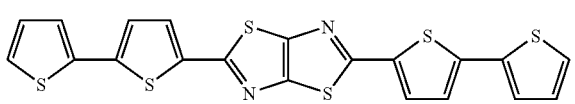

Formula 3

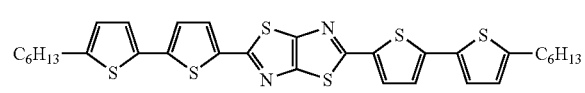

Formula 4

SUMMARY

According to an aspect of the invention, there is provided a thiazolothiazole derivative represented by the following Formula (I):

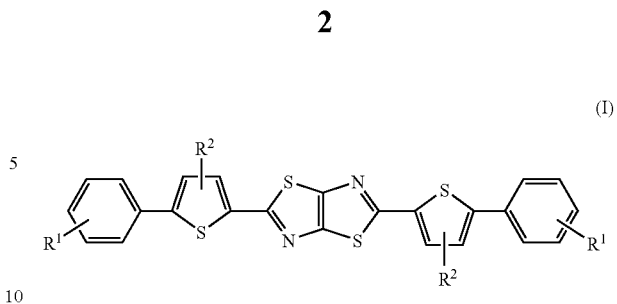

(I)

In Formula (I), each $R^1$ independently represents a straight chain alkyl group having 3 to 20 carbon atoms, a straight chain alkoxy group having 3 to 20 carbon atoms, a branched alkyl group having 3 to 20 carbon atoms, or a branched alkoxy group having 3 to 20 carbon atoms; and each $R^2$ independently represents a hydrogen atom, a straight chain alkyl group having 1 to 20 carbon atoms, a straight chain alkoxy group having 1 to 20 carbon atoms, a branched alkyl group having 3 to 20 carbon atoms, or a branched alkoxy group having 3 to 20 carbon atoms.

BRIEF DESCRIPTION OF THE DRAWINGS

Exemplary embodiments of the present invention will be described in detail based on the following figures, wherein.

DETAILED DESCRIPTION

Figure 1:
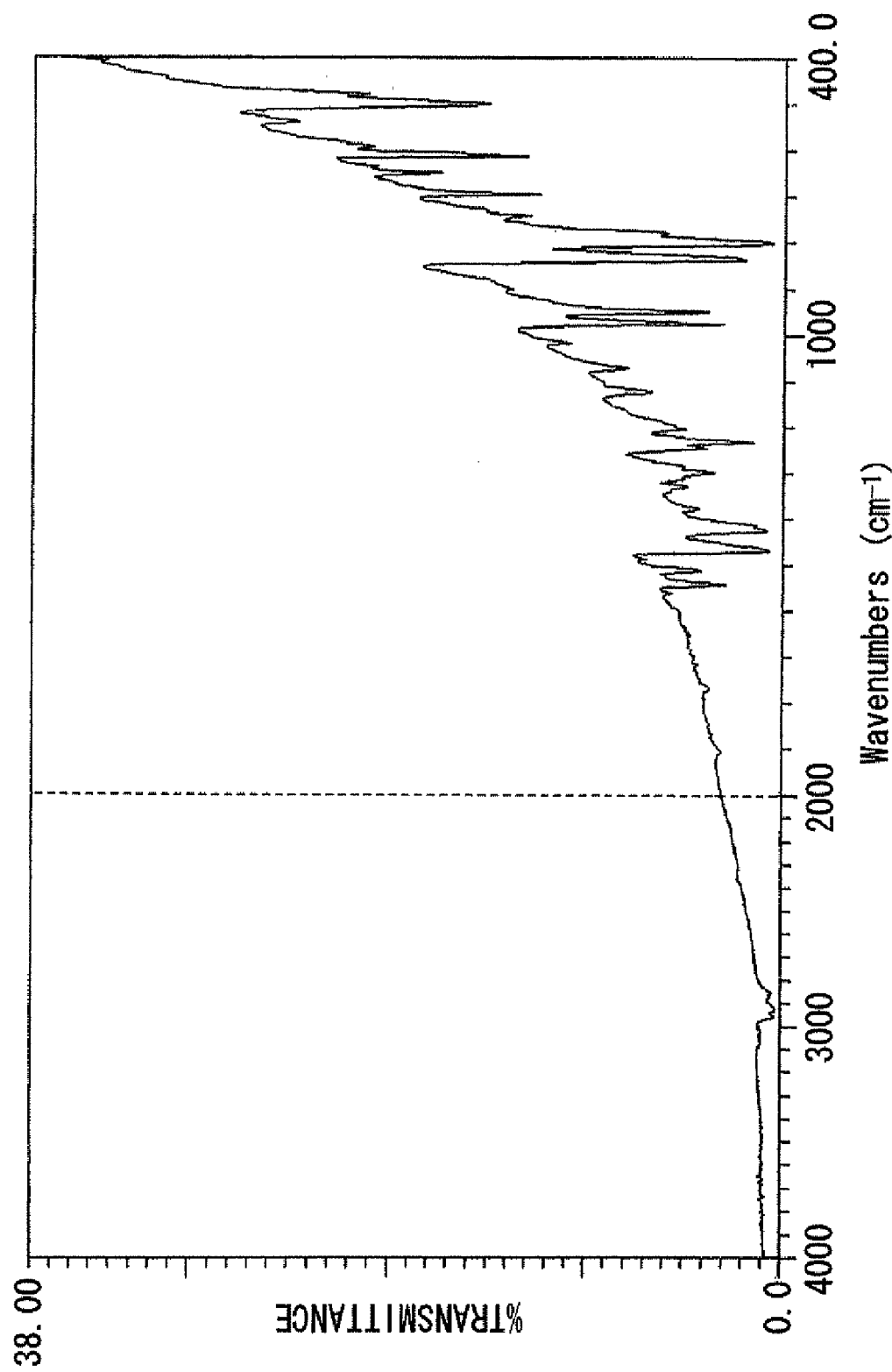
FIG. 1 shows an infrared absorption spectrum in Example 1.

The thiazolothiazole derivative according to the present exemplary embodiment is represented by the following Formula (I).

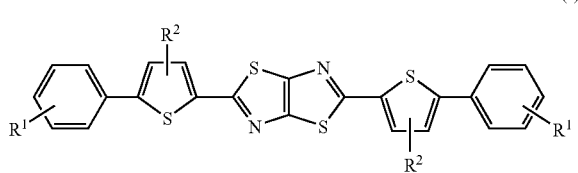

(I)

In Formula (I), each $R^1$ independently represents a straight chain alkyl group having 3 to 20 carbon atoms, a straight chain alkoxy group having 3 to 20 carbon atoms, a branched alkyl group having 3 to 20 carbon atoms, or a branched alkoxy group having 3 to 20 carbon atoms; each $R^2$ independently represents a hydrogen atom, a straight chain alkyl group having 1 to 20 carbon atoms, a straight chain alkoxy group having 1 to 20 carbon atoms, a branched alkyl group having 3 to 20 carbon atoms, or a branched alkoxy group having 3 to 20 carbon atoms.

In a preferable example of the compound represented by Formula (I), each $R^1$ independently represents a straight chain substituent having 3 to 12 carbon atoms or a branched substituent having a main chain portion composed of 3 to 12 carbon atoms, and each $R^2$ independently represents a straight chain substituent having 1 to 12 carbon atoms or a branched substituent having a main chain portion composed of 2 to 12 carbon atoms.

The straight chain substituent having 3 to 12 carbon atoms may be a straight chain alkyl group having 3 to 12 carbon atoms or a straight chain alkoxy group having 3 to 12 carbon atoms. The branched substituent having a main chain portion composed of 3 to 12 carbon atoms may be a branched alkyl group having 3 to 20 carbon atoms in which a main chain portion—a straight chain portion excluding the branched chain or branched chains of the branched alkyl group—has 2 to 12 carbon atoms, or a branched alkoxy group having 3 to 20 carbon atoms in which a main chain portion—a straight chain portion excluding the branched chain or branched chains of the branched alkoxy group—has 2 to 12 carbon atoms.

It is considered that the thiazolothiazole derivative of the present exemplary embodiment has excellent charge transporting properties due to high planarity of the aromatic ring in the chemical structure and extended conjugation of π electrons.

Since the compound represented by Formula (I) has phenyl groups as substituents adjacent to thiophene rings, the compound has improved solubility. It is presumed that the following mechanisms work:

the improved solubility is achieved due to free rotation of the bond between each thiophene ring and the terminal phenyl substituent adjacent thereto;

incorporation of an alkyl group or an alkoxy group as $R^1$ increases hydrophobic interactions between the compound of Formula (I) and an organic solvent, thereby increasing the solubility in the organic solvent;

incorporation of an alkyl group or an alkoxy group as $R^2$ increases hydrophobic interactions between the compound of Formula (I) and an organic solvent, thereby greatly increasing the solubility in the organic solvent; ionic potential is also decreased thereby;

incorporation of an alkyl group or an alkoxy group as a substituent on a phenyl group increases the molecular weight, thereby providing high thermal stability; and in particular, when the lengths of the substituents $R^1$ and $R^2$ in the Formula (I) of the thiazolothiazole derivative are controlled by selecting each of the substituents from an alkyl or alkoxy group having 20 or less carbon atoms, preferably from an alkyl or alkoxy group having 12 or less carbon atoms, and in the case of $R^2$, still more preferably selecting from an alkyl or alkoxy group having 8 or less carbon atoms, the intertwining of the substituents may be prevented, thereby increasing the solubility.

The presumptions described above should not be construed as limiting the present exemplary embodiment.

The thiazolothiazole compound represented by the following Formula 3, which is outside the scope of the compound of the present exemplary embodiment, can be obtained in the form of a crystal. Since the compound represented by Formula 3 hardly dissolves in organic solvents, coating liquids containing the compound represented by Formula 3 cause precipitation, and the coating liquids are unsuitable for practical use due to their poor stability over time. When a layer is formed using the thiazolothiazole compound represented by Formula 3, the thickness of the layer becomes uneven. In contrast, when a layer is formed using the thiazolothiazole compound represented by Formula (I), unevenness in the layer thickness after coating may be suppressed.

Formula 3

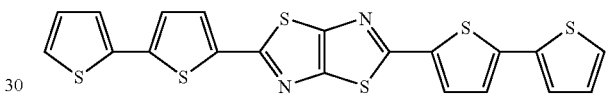

Formula (I) according to the present exemplary embodiment is described in detail below. The position in the phenyl group at which $R^1$ binds to the phenyl group is preferably the 3-position or the 4-position, and is more preferably the 4-position.

When $R^1$ represents a straight chain alkyl group having 3 to 20 carbon atoms, specific examples thereof include a propyl group, a butyl group, a hexyl group, an octyl group, a decyl group, a dodecyl group, a tetradecyl group, a hexadecyl group, an octadecyl group, and an icosyl group. The straight chain alkyl group having 3 to 20 carbon atoms is preferably a straight chain alkyl group having 3 to 12 carbon atoms, and examples thereof include a propyl group, a butyl group, a hexyl group, an octyl group, a decyl group, and a dodecyl group; the straight chain alkyl group having 3 to 12 carbon atoms is preferably a butyl group, a hexyl group, an n-octyl group, or a dodecyl group.

When $R^1$ represents a straight chain alkoxy group having 3 to 20 carbon atom, specific examples thereof include a propoxy group, a butoxy group, a hexyloxy group, an octyloxy group, a decyloxy group, a dodecyloxy group, a tetradecyloxy group, a hexadecyloxy group, an octadecyloxy group, and an icosyloxy group. The straight chain alkoxy group having 3 to 20 carbon atom is preferably a straight chain alkoxy group having 3 to 12 carbon atoms, and examples thereof include a propoxy group, a butoxy group, a hexyloxy group, an octoxy group, an octyloxy group, a decyloxy group, and a dodecyloxy group; the straight chain alkoxy group having 3 to 12 carbon atoms is preferably a butoxy group, a hexyloxy group, an octoxy group, or dodecyloxy group.

When $R^1$ represents a branched alkyl group having 3 to 20 carbon atoms, specific examples thereof include an isopropyl group, an isobutyl group, a sec-butyl group, a tert-butyl group, an isopentyl group, tert-pentyl group, a 1-methylpentyl group, a 4-methylpentyl group, a 3,3-dimethylbutyl group, a 2-ethylbutyl group, a 1-methylhexyl group, a tert-octyl group, a 1-methylheptyl group, a 2-ethylhexyl group, a 2-propylpentyl group, a 2,2-dimethylhexyl group, a 2-methyloctyl group, a 2,2-dimethylheptyl group, a 2,2-dimethyloctyl group, a 2,3-dimethyloctyl group, a 2,6-dimethyl-4-heptyl group, a 3,5,5-trimethylhexyl group, a 1-methyldecyl group, a 2-methyldecyl group, a 2,2-dimethyldecyl group, a 2,3-dimethyldecyl group, a 2,2-diethyldecyl group, a 1-hexylheptyl group, a 1-methyhexadecyl group, and a 1,1-dimethylhexadecyl group. The branched alkyl group having 3 to 20 carbon atoms is preferably a branched alkyl group having 3 to 12 carbon atoms, and examples thereof include an isopropyl group, a tert-butyl group, a 2-methylhexyl group, a 2,2-dimethylhexyl group, a 2-methyloctyl group, a 2,2-dimethyloctyl group, a 2,3-dimethyloctyl group, a 2-methyldecyl group, a 2,2-dimethyldecyl group, and a 2,3-dimethyldecyl group. The branched alkyl group having 3 to 12 carbon atoms is preferably a tert-butyl group, a 2,2-dimethylhexyl group, a 2-methyloctyl group, a 2,2-dimethyloctyl group, a 2,3-dimethyloctyl group, or a 2,2-dimethyldecyl group.

When $R^1$ represents a branched alkoxy group having 3 to 20 carbon atoms, specific examples thereof include an isopropoxy group, an isobutoxy group, a sec-butoxy group, a tert-butoxy group, a 3,3-dimethylbutyloxy group, a 2-ethylbutyloxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, a 2,3-dimethyldecyloxy group, a 2-methyldodecyl group, a 2-methyltetradecyl group, a 2-methylhexadecyl group, and a 2-methyloctadecyl group. The branched alkoxy group having 3 to 20 carbon atoms is preferably a branched alkoxy group having 3 to 12 carbon atoms, and examples thereof include an isopropoxy group, a tert-butoxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, and a 2,3-dimethyldecyloxy group. The branched alkoxy group having 3 to 12 carbon atoms is preferably a tert-butoxy group, a 2-methyloctyloxy group, a 2,2-dimethyloctyloxy group, or a 2,3-dimethyldecyloxy group.

When $R^2$ represents a straight chain alkyl group having 1 to 20 carbon atoms, specific examples thereof include a methyl group, an ethyl group, a propyl group, a butyl group, a hexyl group, an octyl group, a decyl group, a dodecyl group, a tetradecyl group, a hexadecyl group, an octadecyl group, and an icosyl group. The straight chain alkyl group having 1 to 20 carbon atoms is preferably a straight chain alkyl group having 1 to 8 carbon atoms, and examples thereof include a methyl group, an ethyl group, a propyl group, a butyl group, a hexyl group, and an octyl group; more preferable examples thereof include a methyl group, a butyl group, a hexyl group, and an octyl group. Further, still more preferable examples thereof include a straight chain alkyl group having 3 to 8 carbon atoms, and examples thereof include a propyl group, a butyl group, a hexyl group, and an octyl group.

When $R^2$ represents a straight chain alkoxy group having 1 to 20 carbon atoms, specific examples thereof include a methoxy group, an ethoxy group, a propoxy group, a butoxy group, a hexyloxy group, an octyloxy group, a decyloxy group, a dodecyloxy group, a tetradecyloxy group, a hexadecyloxy group, an octadecyloxy group, and an icosyloxy group. The straight chain alkoxy group having 1 to 20 carbon atom is preferably a straight chain alkoxy group having 1 to 8 carbon atoms, and examples thereof include a methoxy group, an ethoxy group, a propoxy group, a butoxy group, a hexyloxy group, and an octyloxy group; more preferable examples thereof include a methoxy group, a butoxy group, and a hexyloxy group. Further, still more preferable examples thereof include a straight chain alkoxy group having 3 to 8 carbon atoms, and examples thereof include a butoxy group and a hexyloxy group.

When $R^2$ represents a branched alkyl group having 3 to 20 carbon atoms, specific examples thereof include an isopropyl group, an isobutyl group, a sec-butyl group, a tert-butyl group, an isopentyl group, a tert-pentyl group, a 1-methylpentyl group, a 4-meihylpentyl group, a 3,3-dimethylbutyl group, a 2-ethylbutyl group, a 1-methylhexyl group, a tert-octyl group, a 1-methylheptyl group, a 2-ethylhexyl group, a 2-propylpentyl group, a 2,2-dimethylhexyl group, a 2-methyloctyl group, a 2,2-dimethylheptyl group, a 2,2-dimethyloctyl group, a 2,3-dimethyloctyl group, a 2,6-dimethyl-4-heptyl group, a 3,5,5-trimethylhexyl group, a 1-methyldecyl group, a 2-methyldecyl group, a 2,2-dimethyldecyl group, a 2,3-dimethyldecyl group, a 2,2-diethyldecyl group, a 1-hexylheptyl group, a 1-methylhexadecyl group, and a 1,1-dimethylhexadecyl group. The branched alkyl group having 3 to 20 carbon atoms is preferably a branched alkyl group having 3 to 12 carbon atoms, and examples thereof include an isopropyl group, a tert-butyl group, a 2-methylhexyl group, a 2,2-dimethylhexyl group, a 2-methyloctyl group, a 2,2-dimethyloctyl group, a 2,3-dimethyloctyl group, a 2-methyldecyl group, a 2,2-dimethyldecyl group, and a 2,3-dimethyldecyl group. The branched alkyl group having 3 to 12 carbon atoms is preferably a tert-butyl group, a 2,2-dimethylhexyl group, a 2-methyloctyl group, a 2,2-dimethyloctyl group, a 2,3-dimethyloctyl group, or a 2,2-dimethyldecyl group. Further, still more preferable examples thereof include a branched alkyl group having 3 to 8 carbon atoms, and examples thereof include a tert-butyl group and a 2,2-dimethylhexyl group.

When $R^2$ represents a branched alkoxy group having 3 to 20 carbon atoms, specific examples thereof include an isopropoxy group, an isobutoxy group, a sec-butoxy group, a tert-butoxy group, a 3,3-dimethylbutyloxy group, a 2-ethylbutyloxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, a 2,3-dimethyldecyloxy group, a 2-methyldodecyl group, a 2-methyltetradecyl group, a 2-methylhexadecyl group, or a 2-methyloctadecyl group. The branched alkoxy group having 3 to 20 carbon atoms is preferably a branched alkoxy group having 3 to 12 carbon atoms, and examples thereof include an isopropoxy group, a tert-butoxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, or a 2,3-dimethyldecyloxy group. The branched alkoxy group having 3 to 12 carbon atoms is preferably a tert-butoxy group, a 2-methyloctyloxy group, a 2,2-dimethyloctyloxy group, or a 2,3-dimethyldecyloxy group. Further, still more preferable examples thereof include a branched alkoxy group having 3 to 8 carbon atoms, and examples thereof include a tert-butoxy group and an isopropoxy group.

It is preferable that in Formula (I), each $R^1$ independently represents a straight chain alkyl group having 3 to 20 carbon atoms, a straight chain alkoxy group having 3 to 20 carbon atoms, a branched alkyl group having 3 to 20 carbon atoms, or a branched alkoxy group having 3 to 20 carbon atoms and each $R^2$ independently represents a straight chain alkyl group having 3 to 8 carbon atoms, a straight chain alkoxy group having 3 to 8 carbon atoms, a branched alkyl group having 3 to 8 carbon atoms, or a branched alkoxy group having 3 to 8 carbon atoms, since the resultant thiazolothiazole derivative has excellent solubility not only in halogenated organic solvents, but also in non-halogenated organic solvents. Since the thiazolothiazole derivative having such a structure is easy to produce and purify, it is easy to obtain the thiazolothiazole derivative with high purity. Further, for example, a charge transport material using the thiazolothiazole derivative having such a structure can be easily produced.

In the present exemplary embodiment, the term "dissolve" refers to a state in which, after the thiazolothiazole derivative according to the present exemplary embodiment is added to an organic solvent, no crystal is observed by observation with the naked eye. The term "high solubility" or "good solubility" refers to such properties that the thiazolothiazole derivative dissolves at the boiling temperature of the organic solvent.

The organic solvent used for dissolving the thiazolothiazole derivative of the present exemplary embodiment may be any organic solvent as long as the organic solvent dissolves the thiazolothiazole derivative of the present exemplary embodiment. Examples thereof include common organic solvents such as methanol, ethanol, n-propanol, isopropylalcohol, n-butanol, benzylalcohol, methylcellosolve, ethylcellosolve, acetone, methyl ethyl ketone, cyclohexanone, methyl acetate, n-butyl acetate, dioxane, tetrahydrofuran, diethylether, totuene, xylene, mesitylene, dimethylformamide, dimethylacetamide, and dimethylsulfoxide, and the halogenated organic solvents described below. The organic solvent may be used singly, or in combination of two or more thereof.

Examples of the halogenated organic solvents include a hydrocarbon compound having at least one halogen atom such as a fluorine, chlorine, bromine, or iodine atom, and an aromatic hydrocarbon compound having at least one halogen atom such as a fluorine, chlorine, bromine, or iodine atom. The halogenated organic solvents preferably have a boiling temperature of from 30° C. to 300° C. More preferable examples of the halogenated organic solvents include a hydrocarbon compound having at least one halogen atom and having a boiling temperature of from 50° C. to 200° C., and an aromatic hydrocarbon compound having at least one halogen atom and having a boiling temperature of from 50° C. to 200° C.

Specific examples of the halogenated organic solvents include halogenated hydrocarbons such as chloroform, carbon tetrachloride, and dichloroethylene, and halogenated aromatic hydrocarbons such as chlorobenzene, dichlorobenzene, trichlorobenzene, chloromethylbenzene, o-chlorotoluene, o-,p-dichlorotoluene, and trichlorotoluene.

The thiazolothiazole derivative represented by Formula (I) may be synthesized, for example, as described below. However, the process for synthesizing the thiazolothiazole derivative is not limited thereto.

(1) A process in which the 5-position of each thiophene ring adjacent to the thiazolothiazole moiety is halogenated, and the obtained halogenated compound is subjected to a Suzuki reaction with an alkyl- or alkoxy-substituted phenyl boric acid or a pinacol boron.

(2) A process in which thiophene boric acid is subjected to a Suzuki reaction with an alkyl- or alkoxy-substituted bromophenyl so as to synthesize an alkyl- or alkoxy-substituted phenylthiophene, and the 5-position of the alkyl- or alkoxy-substituted phenylthiophene is formylated, which is then reacted with rubeanic acid or the like to cause cyclization.

The process of item (2) is the method described in Japanese Patent Application Laid-Open (JP-A) No. 2006-206503. When this method is used, the formylated compound as a reaction intermediate has poor stability, and decomposes during reaction at high temperatures (specifically 200° C. or higher); further the solubility of the reaction product is low, so that purification thereof is difficult. Moreover, since the formylated compound as a reaction intermediate decomposes during reaction, recovery of the raw materials is difficult and the yield of the reaction is small, thereby increasing the cost.

In contrast, in the reaction of item (1), a thiophene-containing thiazolothiazole skeleton is prepared first, the 5-position of each thiophene ring is halogenated, and terminal substituents are introduced through a Suzuki reaction with an alkyl- or alkoxy-substituted phenyl boric acid or a pinacol boron. In this process, purification can be conducted at the respective stages, the compounds involved in the process are stable, and the yield of the reaction is high.

The method of producing the thiazolothiazole derivative is described specifically below. In the present exemplary embodiment, for example, rubeanic acid and the thiophene aldehyde derivative represented by the following Formula (II-1) are reacted with each other to cause cyclization, whereby a thiophene-containing thiazolothiazole (the following Formula (III-1)) is synthesized. Regarding this reaction, the method described in J. R. Johnson, D. H. Rotenberg, and R. Ketcham, *J. Am. Chm. Soc.*, vol. 92, 4096 (1970) may be referenced. Thereafter, the thiophene-containing thiazolothiazole is halogenated, for example by a known method using N-bromosuccinimide (hereinafter referred to as NBS), so that a halogen compound represented by the following Formula (IV-1) is synthesized. The obtained compound is further subjected to a Suzuki coupling reaction with a substituted phenyl boric acid or substituted phenyl pinacol boron represented by the following Formula (V-1) in the presence of a palladium catalyst, whereby a thiazolothiazole derivative represented by Formula (I) is synthesized.

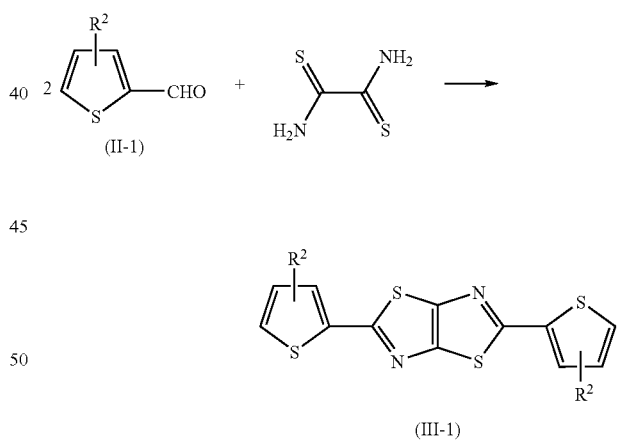

$R^2$ in Formula (II-1) and $R^2$ in Formula (III-1) each have the same definition as that of $R^2$ in Formula (I).

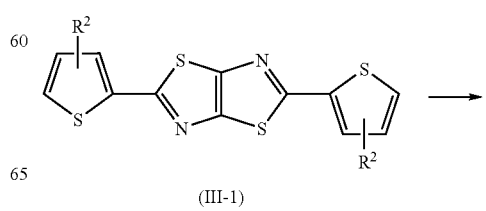

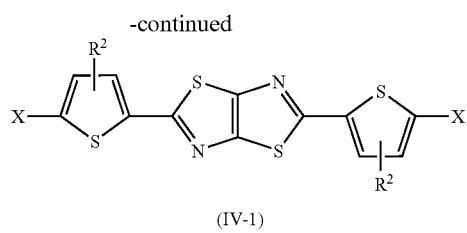

(IV-1)

In Formula (IV-1), $R^2$ has the same definition as that of $R^2$ in Formula (I), and X represents a bromine atom or an iodine atom.

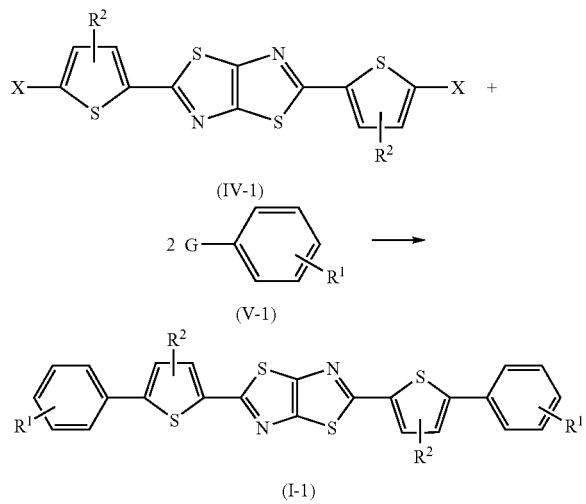

In Formula (V-1), $R^1$ has the same definition as that of $R^1$ in Formula (I-1), and G represents a boric acid group or a boric ester group.

The boric ester group is preferably, for example, a boric acid pinacolate ester group, a boric acid 1,3-propanediol ester group, or a boric acid neopentylglycol ester group, from the viewpoint of easily obtaining the reagents.

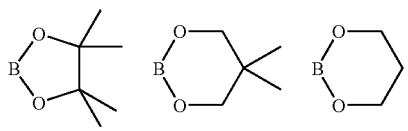

In the following, synthesis examples for some specific compounds are shown. The other specific compounds may be synthesized in similar manners. The synthesis methods are not limited thereto.

Identification of the obtained product is performed using $^1$H-NMR spectrum ($^1$H-NMR, using CDCl$_3$ as the solvent and a UNITY-300 manufactured by VARIAN Inc. at 300 MHz) and IR spectrum (KBr tablet method, using a Fourier transformation infrared spectrophotometer FT-730 at a resolution of 4 cm$^{-1}$ manufactured by Horiba Ltd.)

Specific compounds according to the present exemplary embodiment include, but are not limited to, those shown below.

| No. | R$^1$ Structure | R$^1$ Bond Position | R$^2$ Structure | R$^2$ Bond Position |
|---|---|---|---|---|
| 1 | ~~~CH$_3$ (C4) | 4 | —H | 3 |
| 2 | ~~~CH$_3$ (C5) | 4 | —H | 3 |
| 3 | ~~~CH$_3$ (C6) | 4 | —H | 3 |
| 4 | ~~~CH$_3$ (C7) | 4 | —H | 3 |
| 5 | ~~~CH$_3$ (C10) | 4 | —H | 3 |
| 6 | ~~~CH$_3$ (C4) | 4 | —H | 3 |
| 7 | ~~~CH$_3$ (C4) | 4 | —CH$_3$ | 3 |
| 8 | ~~~CH$_3$ (C7) | 4 | —CH$_3$ | 3 |
| 9 | ~~~CH$_3$ (C10) | 4 | —CH$_3$ | 3 |
| 10 | —O—CH$_3$ | 4 | —O—CH$_3$ | 3 |

-continued

| No. | R¹ Structure | R¹ Bond Position | R² Structure | R² Bond Position |
|---|---|---|---|---|
| 11 | —O—CH₂—CH₂—CH₃ | 4 | —H | 3 |
| 12 | —O—(CH₂)₄—CH₃ | 4 | —(CH₂)₃—CH₃ | 3 |
| 13 | —O—(CH₂)₅—CH₃ | 4 | —CH₃ | 3 |
| 14 | —O—(CH₂)₉—CH₃ | 4 | 3-methylhexyl (H₃C-CH(-)-(CH₂)₃-CH₃ with ethyl) | 3 |
| 15 | —C(CH₃)₃ (tert-butyl) | 4 | —H | 3 |
| 16 | 3-methyl-3-ethyl-hexyl | 4 | 3-methylpentyl (H₃C-CH(-)-CH₂-CH₃ with ethyl) | 3 |
| 17 | 3-methylheptyl (with ethyl branch) | 4 | —O—CH₂—CH(CH₃)—CH₂—CH₃ | 3 |
| 18 | —O—CH₂—C(CH₃)(C₂H₅)—(CH₂)₄—CH₃ | 4 | —O—(CH₂)₂—CH₃ | 3 |
| 19 | —O—C(CH₃)₃ | 4 | —O—(CH₂)₃—CH₃ | 3 |

-continued

| No. | R¹ Structure | R¹ Bond Position | R² Structure | R² Bond Position |
|---|---|---|---|---|
| 20 | —O—CH₂—C(CH₃)(H)—CH(CH₃)—C₆H₁₂—CH₃ (branched ether structure) | 4 | —CH₃ | 3 |
| 21 | C₂H₅—C(CH₃)(CH₃)—C₅H₁₀—CH₃ (branched alkyl) | 4 | —H | 3 |
| 22 | C₂H₅—C(CH₃)(CH₃)—C₆H₁₂—CH₃ (branched alkyl) | 4 | hexyl (—C₅H₁₀—CH₃) | 3 |
| 23 | C₂H₅—C(CH₃)(CH₃)—C₈H₁₆—CH₃ (branched alkyl) | 4 | —CH₃ | 3 |
| 24 | —O—CH₂—C(CH₃)(H)—C₅H₁₀—CH₃ (branched ether) | 4 | —O—CH(CH₃)₂ | 3 |
| 25 | pentyl (—C₄H₈—CH₃) | 4 | heptyl (—C₆H₁₂—CH₃) | 3 |
| 26 | heptyl (—C₆H₁₂—CH₃) | 4 | octyl (—C₇H₁₄—CH₃) | 3 |
| 27 | nonyl (—C₈H₁₆—CH₃) | 4 | nonyl (—C₈H₁₆—CH₃) | 3 |
| 28 | undecyl (—C₁₀H₂₀—CH₃) | 4 | nonyl (—C₈H₁₆—CH₃) | 3 |
| 29 | —O—CH₂—CH₂—CH₃ | 4 | nonyl (—C₈H₁₆—CH₃) | 3 |
| 30 | —O—CH₂—CH₂—CH₂—CH₂—CH₃ | 4 | nonyl (—C₈H₁₆—CH₃) | 3 |

-continued
| | R¹ | | R² | |
|---|---|---|---|---|
| No. | Structure | Bond Position | Structure | Bond Position |
| 31 | 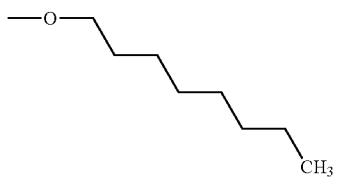 | 4 | 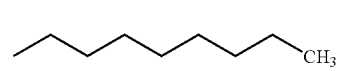 | 3 |
| 32 | 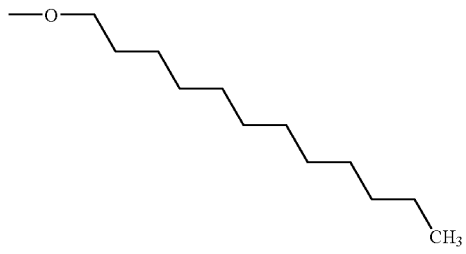 | 4 | 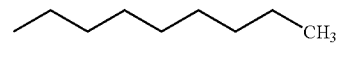 | 3 |
| 33 | 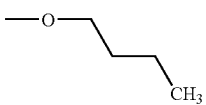 | 2 | 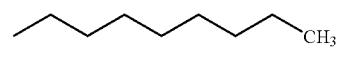 | 3 |
| 34 | 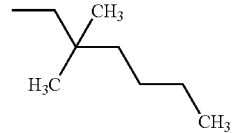 | 2 | 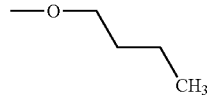 | 3 |
| 35 | 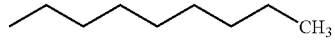 | 2 | 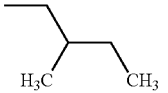 | 3 |
| 36 | 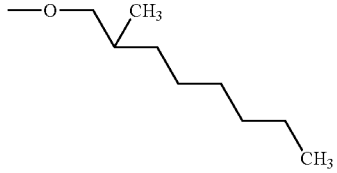 | 2 | —CH₃ | 3 |
| 37 | 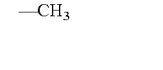 | 3 | 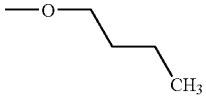 | 3 |
| 38 | 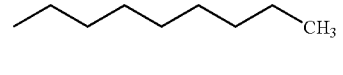 | 3 | 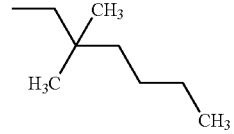 | 3 |
| 39 | 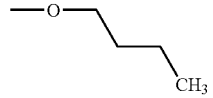 | 3 | 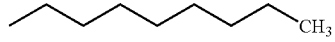 | 3 |

-continued

| | R¹ | | R² | |
|---|---|---|---|---|
| No. | Structure | Bond Position | Structure | Bond Position |
| 40 | 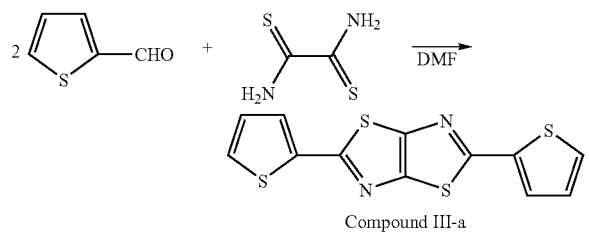 | 3 | —CH₃ | 3 |

EXAMPLES

The present invention is described below by reference to examples. However, the examples should not be construed as limiting the invention.

Example 1

Synthesis of Compound III-a 5.3 g (45 mmol) of rubeanic acid and 20 g (180 mmol) of 2-thiophene aldehyde are put into a 200 ml three-necked flask, and 100 ml of dimethylformamide (hereinafter referred to as DMF) is added thereto, thereby dissolving the substances in the flask. The solution is stirred at 150° C. for 5 hours using a magnetic stirrer, and is cooled to 25° C. The reaction solution is poured into 1 L of pure water in a 2 L beaker, and the resultant mixture is stirred at 25° C. for 30 minutes using a magnetic stirrer. After the completion of the stirring, the precipitated crystal is collected by suction filtration, and washed with 1 L of pure water. The obtained crystal is further washed with 100 ml of methanol, and vacuum-dried at 60° C. for 15 hours. After drying, the crystal is dissolved in 100 ml of tetrahydrofuran (hereinafter referred to as THF), and purified by using a silica gel short column, whereby Compound II-a is obtained in an amount of 6.4 g. The obtained compound is identified as the desired product by ¹H-NMR and IR.

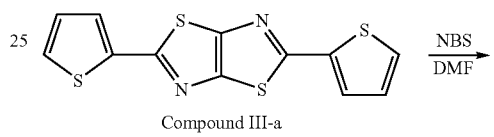

Compound III-a

Synthesis of Compound IV-a

Under nitrogen atmosphere, 4.5 g (15 mmol) of Compound III-a and 8.0 g (45 mmol) of N-bromosuccinimide (hereinafter referred to as NBS) are dissolved in 200 ml of DMF in a 500 ml three-necked flask. The solution is stirred at 60° C. for 7 hours using a magnetic stirrer, thereby completing the reaction. After cooling to 25° C., the reaction solution is poured into 1 L of pure water in a 2 L beaker, and the resultant mixture is stirred at 25° C. for 30 minutes using a magnetic stirrer. After the completion of the stirring, the precipitated crystal is collected by suction filtration, and is washed with 1 L of pure water The crystal is vacuum-dried at 60° C. for 15 hours, and the crystal is subjected to recrystallization from N-methylpyrrolidone (hereinafter referred to as NMP) twice, whereby 3.3 g of Compound IV-a in the form of a yellow crystal is obtained. The obtained compound is identified as the desired product by ¹H-NMR and IR.

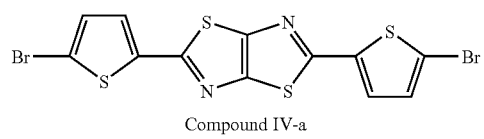

Compound III-a

Compound IV-a

Synthesis of Exemplary Compound 1

Figure 2:
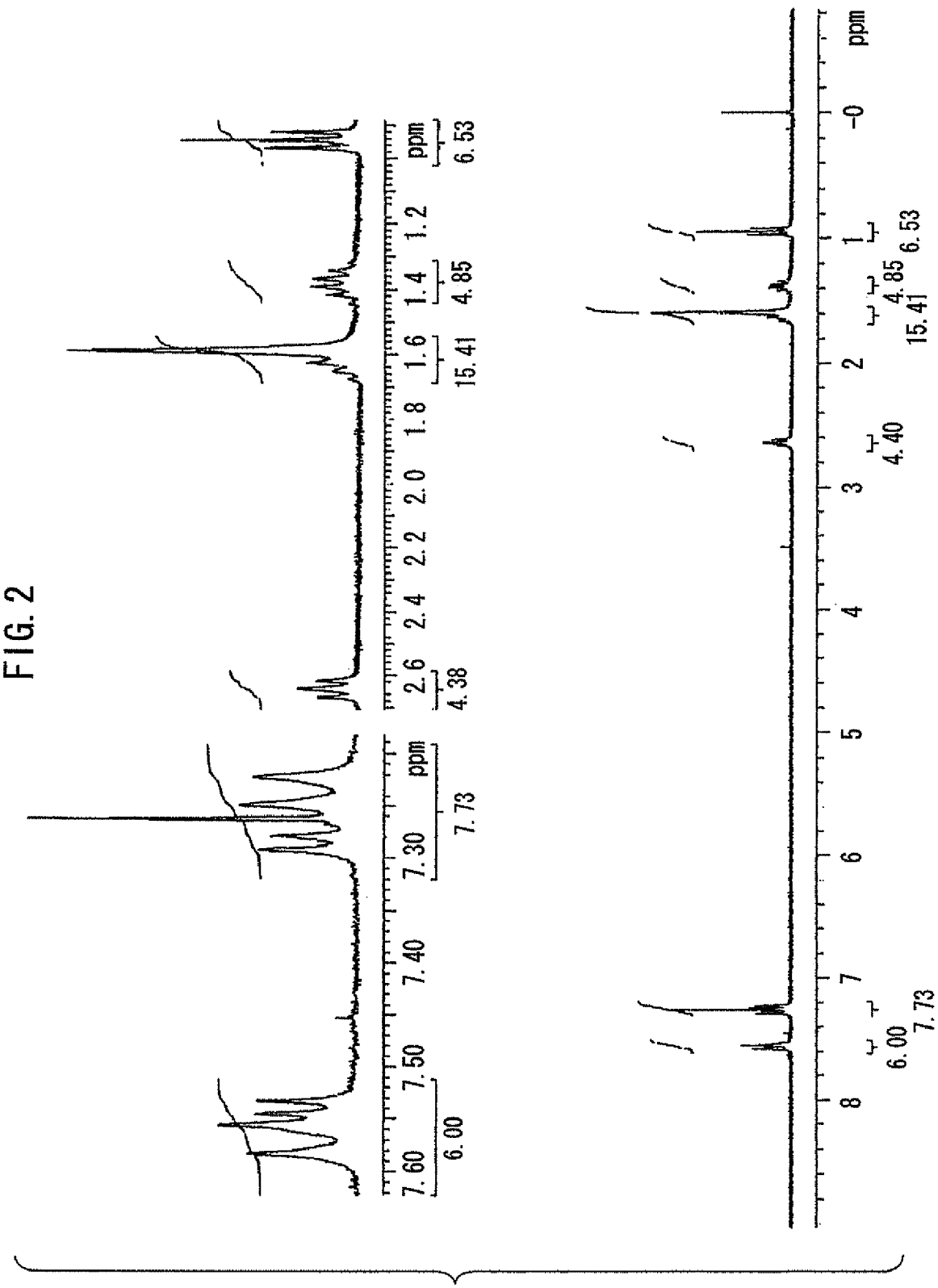
FIG. 2 shows a $^1$H-NMR spectrum in Example 1.

Under nitrogen atmosphere, 0.23 g (0.20 mmol) of tetrakistriphenylphosphine palladium(0) is dissolved in 100 ml of NMP in a 300 ml three-necked flask. 1.84 g (4.0 mmol) of Compound IV-a, 8.0 ml of a 2M sodium carbonate aqueous solution, and 1.56 g (8.8 mmol) of 4-n-butylphenyl borate are sequentially added, in this order, to the solution obtained above. The resultant mixture is refluxed for 5 hours in an oil bath at 220° C. under stirring by a magnetic stirrer. After confirming the completion of the reaction by ¹H-NMR, the reaction solution is cooled to 25° C., and the reaction solution is poured into 1 L of pure water in a 2 L beaker. The resultant mixture in the beaker is stirred at 25° C. for 30 minutes using a magnetic stirrer. After the completion of the stirring, the precipitated crystal is collected by suction filtration, and is washed with 1 L of pure water. The obtained crystal is further washed with 100 ml of methanol, and then with 100 ml of toluene, and then vacuum-dried at 60° C. for 15 hours. 150 ml of NMP is added to the crystal, and recrystallization is performed, followed by purification by sublimation. As the result, Exemplary Compound 1 in the form of an orange crystal is obtained in an amount of 1.0 g. The IR spectrum and ¹H-NMR spectrum of the obtained Exemplary Compound 1 are shown in FIGS. 1 and 2, respectively.

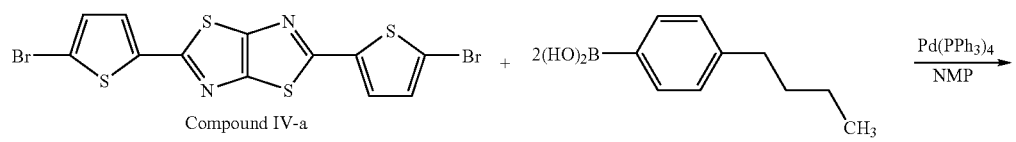

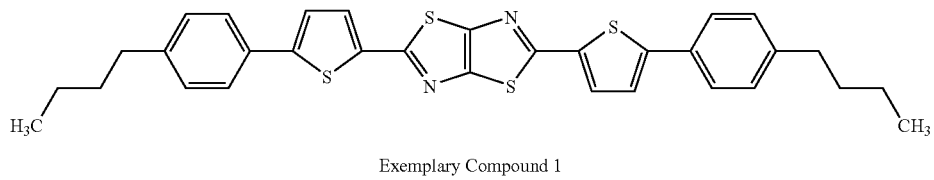

Exemplary Compound 1

Example 2

Synthesis of Exemplary Compound 11

Figure 3:
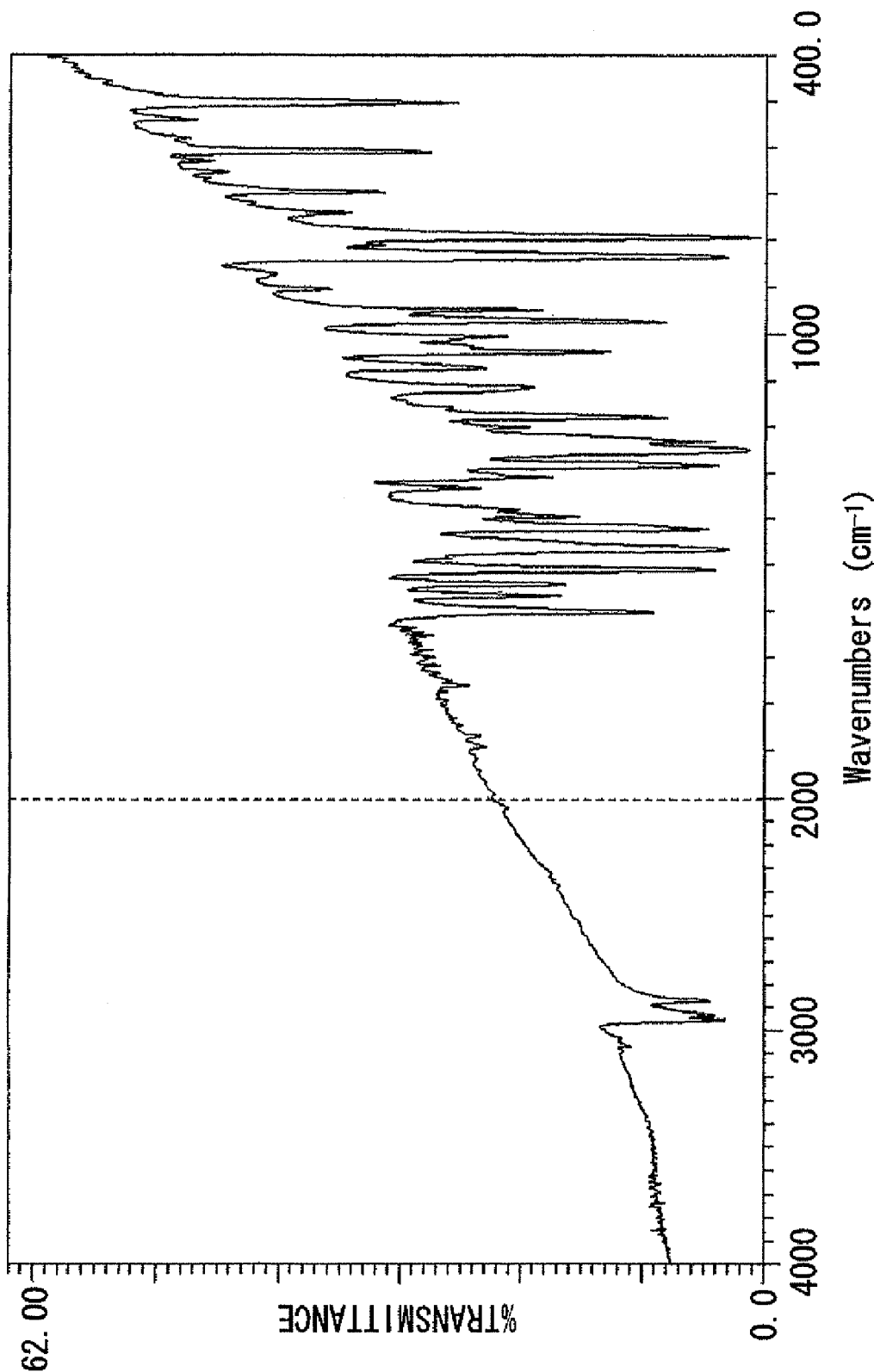
FIG. 3 shows an infrared absorption spectrum in Example 2.
Figure 4:
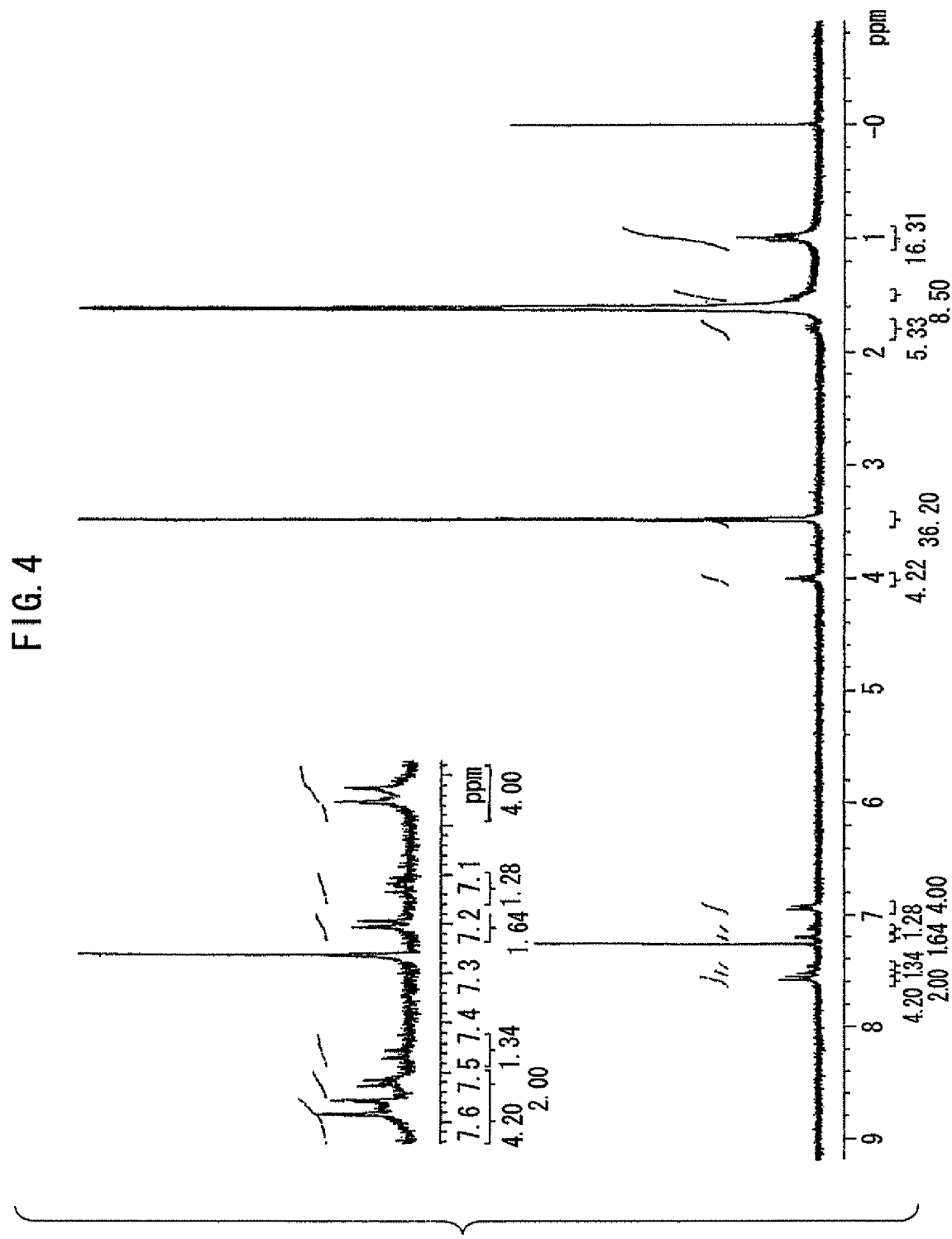
FIG. 4 shows a $^1$H-NMR spectrum in Example 2.

Under nitrogen atmosphere, 0.14 g (0.12 mmol) of tetrakistriphenylphosphine palladium(0) is dissolved in 100 ml of NMP in a 300 ml three-necked flask. 1.85 g (4.0 mmol) of Compound IV-a, 8.0 ml of a 2M sodium carbonate aqueous solution, and 1.71 g (8.8 mmol) of 4-n-butoxyphenyl borate are sequentially added, in this order, to the solution in the flask. The resultant mixture is refluxed for 4 hours in an oil bath at 220° C. under stirring by a magnetic stirrer. The completion of the reaction is confirmed by $^1$H-NMR, the reaction solution is cooled to 25° C., and the reaction solution is poured into 1 L of pure water in a 2 L beaker. The resultant mixture in the beaker is stirred at 25° C. for 20 minutes using a magnetic stirrer. After completion of the stirring, the precipitated crystal is collected by suction filtration, and is washed with 1 L of pure water. The obtained crystal is further washed with 200 ml of methanol, and then with 250 ml of toluene, and then vacuum-dried at 60° C. for 15 hours. 150 ml of NMP is added to the crystal, and recrystallization is performed, followed by purification by sublimation. As the result, Exemplary Compound 11 in the form of an orange crystal is obtained in an amount of 1.0 g. The IR spectrum and $^1$H-NMR spectrum of the obtained Exemplary Compound 11 are shown in FIGS. 3 and 4, respectively.

Example 3

Synthesis of Exemplary Compound 15

Under nitrogen atmosphere, 0.11 g (0.10 mmol) of tetrakistriphenylphosphine palladium(0) is dissolved in 80 ml of NMP in a 300 ml three-necked flask. 1.39 g (3.0 mmol) of Compound IV-a, 6.0 ml of a 2M sodium carbonate aqueous solution, and 1.18 g (6.6 mmol) of 4-tert-butylphenyl borate are sequentially added, in this order, to the solution in the flask. The resultant mixture is refluxed for 5 hours in an oil bath at 220° C. under stirring by a magnetic stirrer. After the completion of the reaction is confirmed by $^1$H-NMR, the reaction mixture is cooled to 25° C., and the reaction mixture is poured into 500 ml of pure water in a 1 L beaker. The resultant mixture is stirred at 25° C. for 30 minutes using a magnetic stirrer After the completion of the stirring, the precipitated crystal is collected by suction filtration, and washed with 500 ml of pure water. The obtained crystal is further washed with 100 ml of methanol, and then with 100 ml of hexane, and then vacuum-dried at 60° C. for 15 hours. 400 ml of monochlorobenzene is added to the crystal, and recrystallization is performed, followed by purification by sublimation. As the result, Exemplary Compound 15 in the form of an orange crystal is obtained in an amount of 1.0 g.

Figure 5:
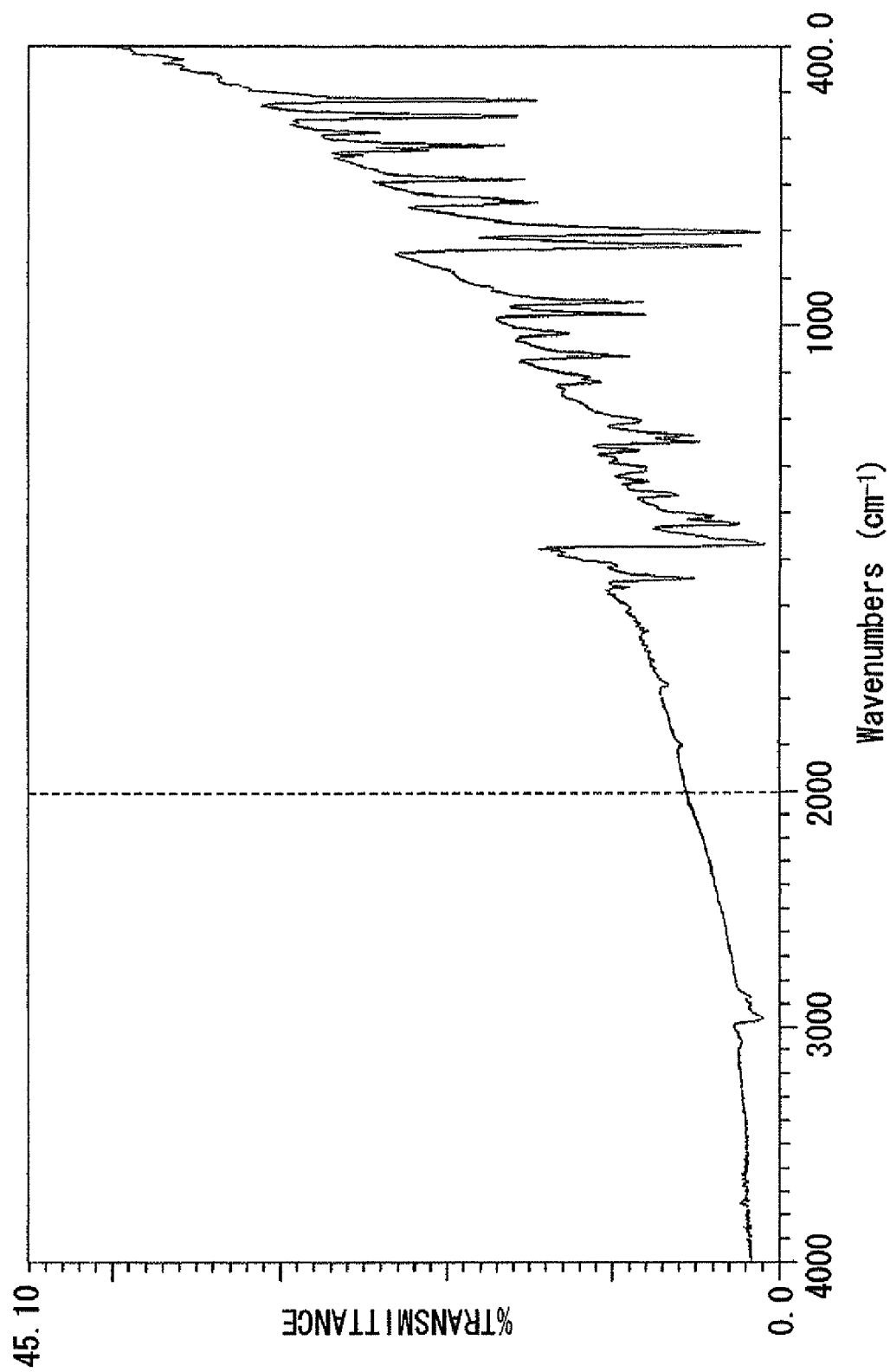
FIG. 5 shows an infrared absorption spectrum in Example 3.
Figure 6:
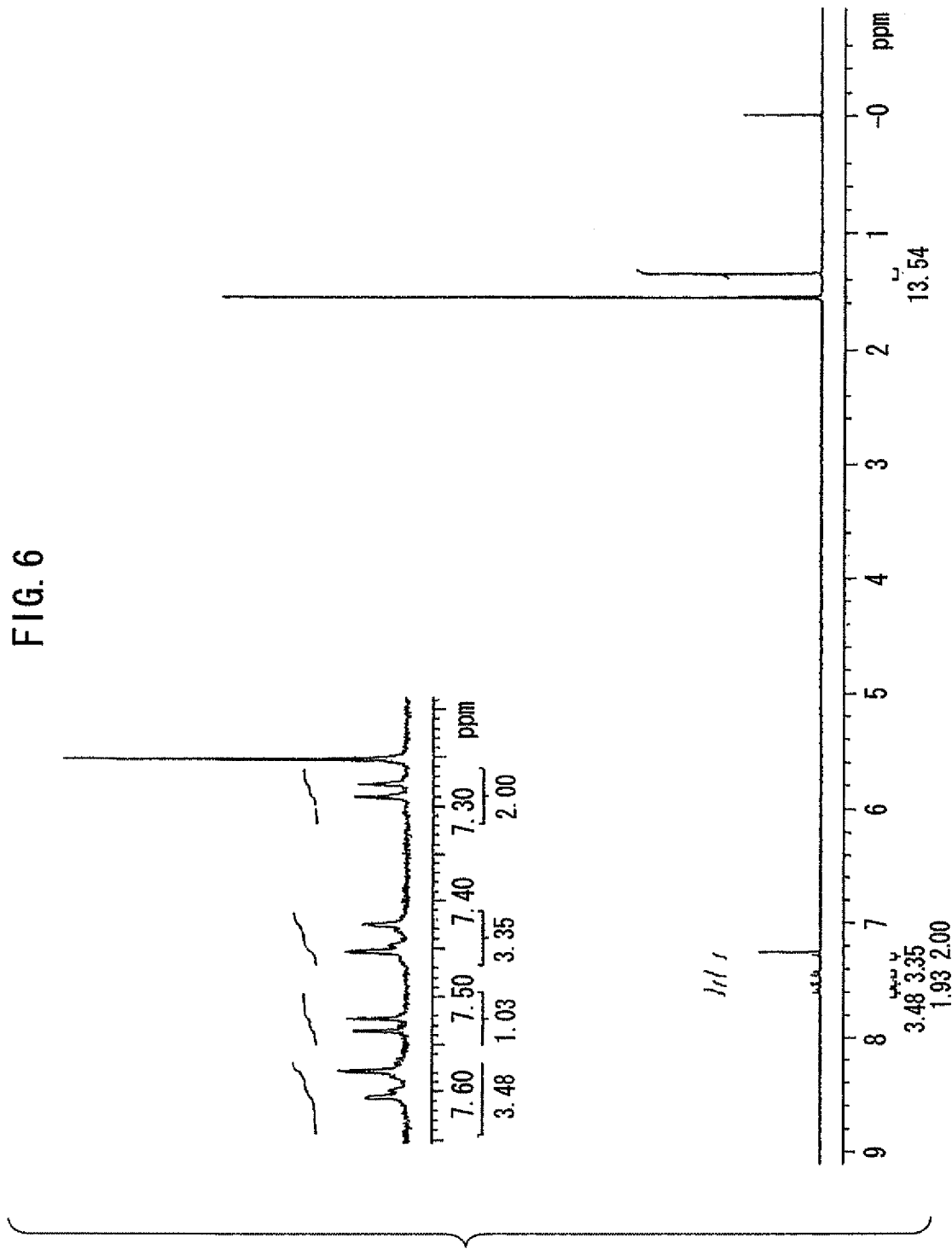
FIG. 6 shows a $^1$H-NMR spectrum in Example 3.

The IR spectrum and $^1$H-NMR spectrum of the obtained Exemplary Compound 15 are shown in FIGS. 5 and 6.

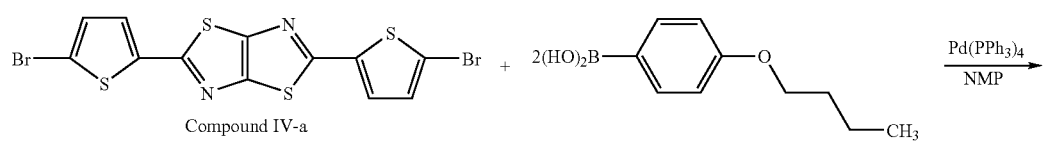

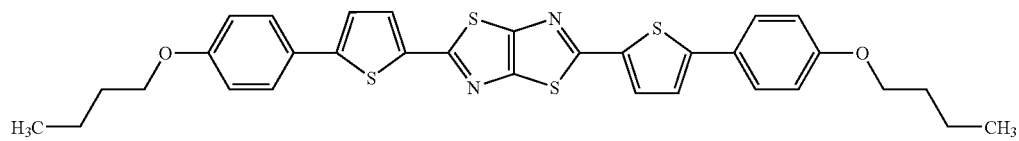

Exemplary Compound 11

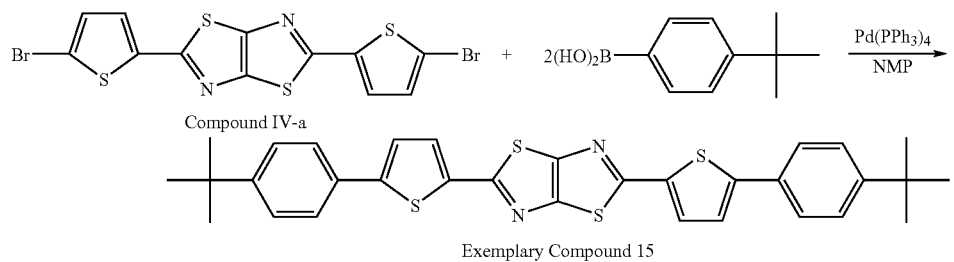

Exemplary Compound 15

Example 4

Synthesis of Compound III-b 18 g (150 mmol) of rubeanic acid and 75 g (600 mmol) of 3-methylthiophene-2-aldehyde are put into a 1 L three-necked flask, and 350 ml of DMF is added thereto, thereby dissolving the substances in the flask. The solution is stirred for 5 hours in an oil bath at 150° C. using a magnetic stirrer, and is cooled to 25° C. The reaction solution is poured into 1 L of pure water in a 2 L beaker, and the resultant mixture is stirred at 25° C. for 30 minutes using a magnetic stirrer. After the completion of the stirring, the precipitated crystal is collected by suction filtration, and is washed with 1 L of pure water. 100 ml of toluene and 200 ml of methanol are added to the obtained black sticky crystal, and the solution is stirred for 10 minutes using ultrasonication and a magnetic stirrer, thereby washing the crystal. The washed crystal is collected by suction filtration, whereby 34 g of a crude crystal is obtained. The crude crystal is further washed with 200 ml of methanol, and vacuum-dried at 60° C. for 15 hours. After drying, the crystal is dissolved in 500 ml of monochlorobenzene, and purified by using a silica gel short column, whereby 19 g of Compound III-b is obtained. The obtained compound is identified as the desired product by ¹H-NMR and IR.

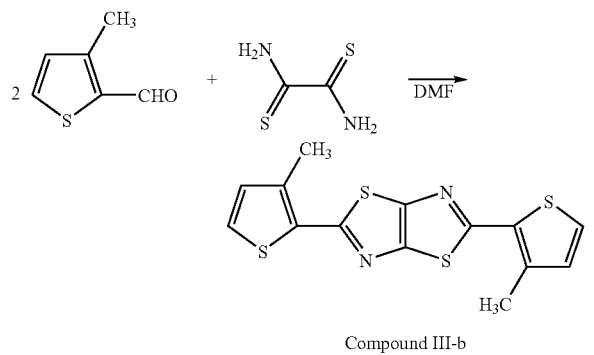

Compound III-b

Synthesis of Compound IV-b

Under nitrogen atmosphere, 19 g (57 mmol) of Compound III-b and 23 g (129 mmol) of NBS are put into a 1 L three-necked flask, and 500 ml of DMF is added thereto, thereby dissolving the substances in the flask. The solution is stirred at 60° C. for 4 hours using a magnetic stirrer, thereby completing the reaction. After cooling to 25° C., the reaction solution is poured into 1 L of pure water in a 2 L beaker, and is stirred at 10° C. for 30 minutes using a magnetic stirrer. After the completion of the stirring, the precipitated crystal is collected by suction filtration and washed with 1 L of pure water and then with 200 ml of methanol. The crystal is vacuum-dried at 60° C. for 15 hours, and then recrystallized twice using 300 ml of NMP, whereby 21 g of Compound IV-b in the form of a yellow crystal is obtained. The obtained compound is identified as the desired product by ¹H-NMR and IR.

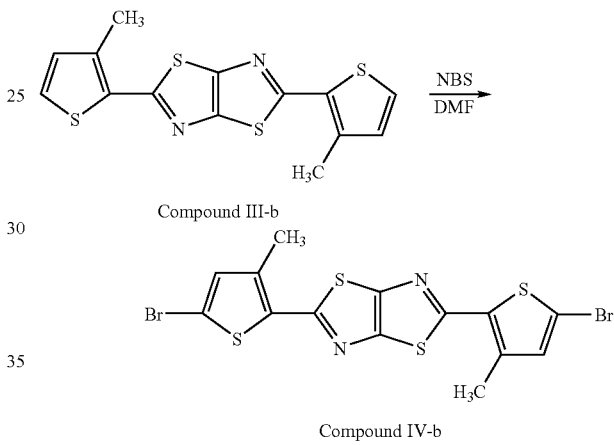

Synthesis of Exemplary Compound 7

Under nitrogen atmosphere, 0.16 g (0.14 mmol) of tetrakistriphenylphosphine palladium(0) is dissolved in 100 ml of NMP in a 300 ml three-necked flask. 2.2 g (4.5 mmol) of Compound IV-b, 9.0 ml of a 2M sodium carbonate aqueous solution, and 1.78 g (10 mmol) of 4-n-butylphenyl borate are sequentially added, in this order, to the solution in the flask. The resultant mixture is refluxed for 6 hours in an oil bath at 220° C. under stirring by a magnetic stirrer. After the completion of the reaction is confirmed by ¹H-NMR, the reaction solution is cooled to 25° C., and the reaction solution is poured into 500 ml of pure water in a 1 L beaker. The resultant mixture in the beaker is stirred at 25° C. for 30 minutes using a magnetic stirrer. After the completion of the stirring, the precipitated crystal is collected by suction filtration, and is washed with 300 ml of pure water. The obtained crystal is further washed with 200 ml of methanol, and then with 100 ml of hexane, and vacuum-dried at 60° C. for 15 hours. The crystal is dissolved in 200 ml THF/100 ml toluene under heating, and purified by using a silica gel short column. Then, the crystal is recrystallized using 300 ml of toluene, whereby 0.70 g of Exemplary Compound 7 in the form of an orange crystal is obtained.

Figure 7:
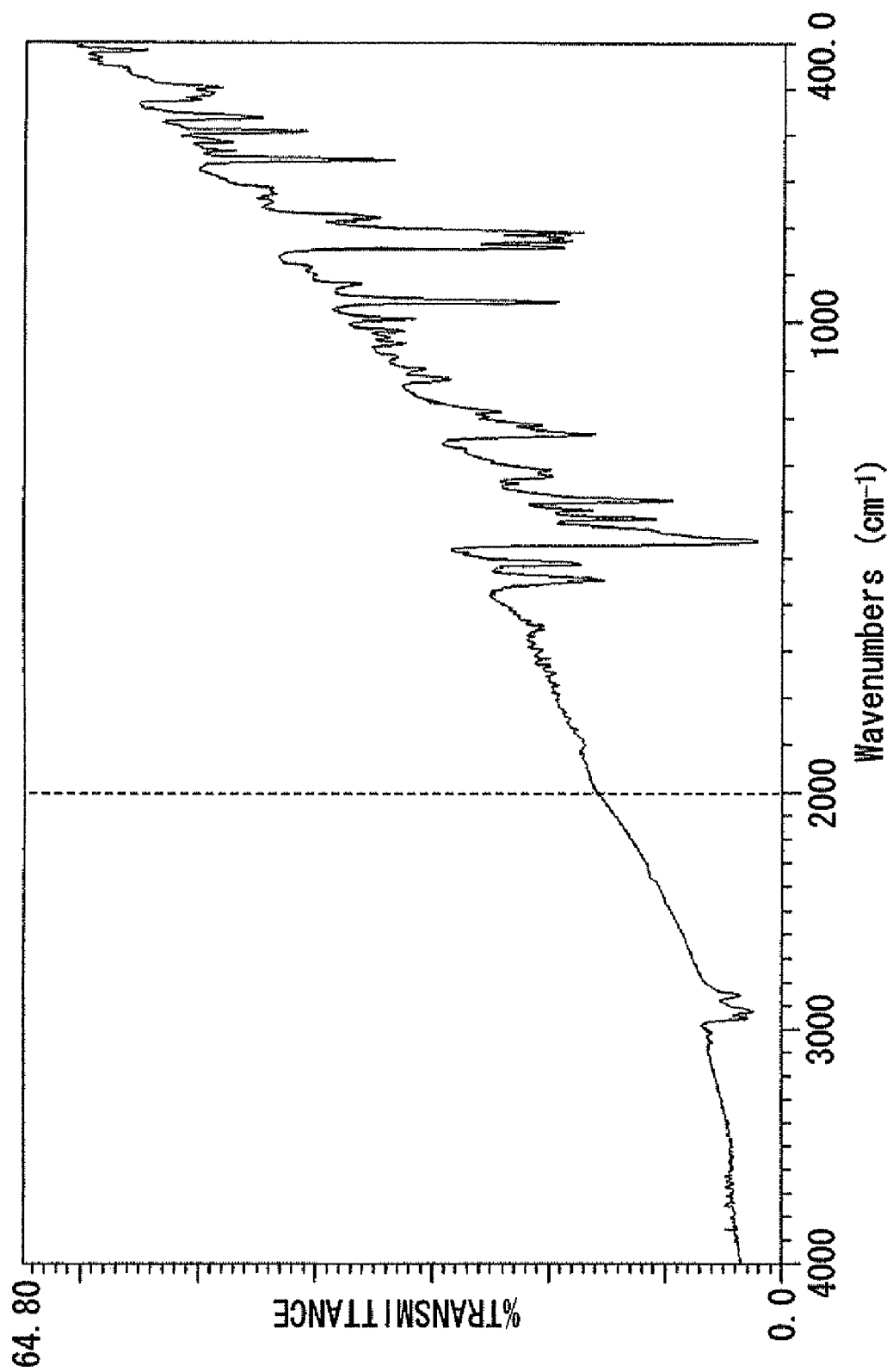
FIG. 7 shows an infrared absorption spectrum in Example 4.
Figure 8:
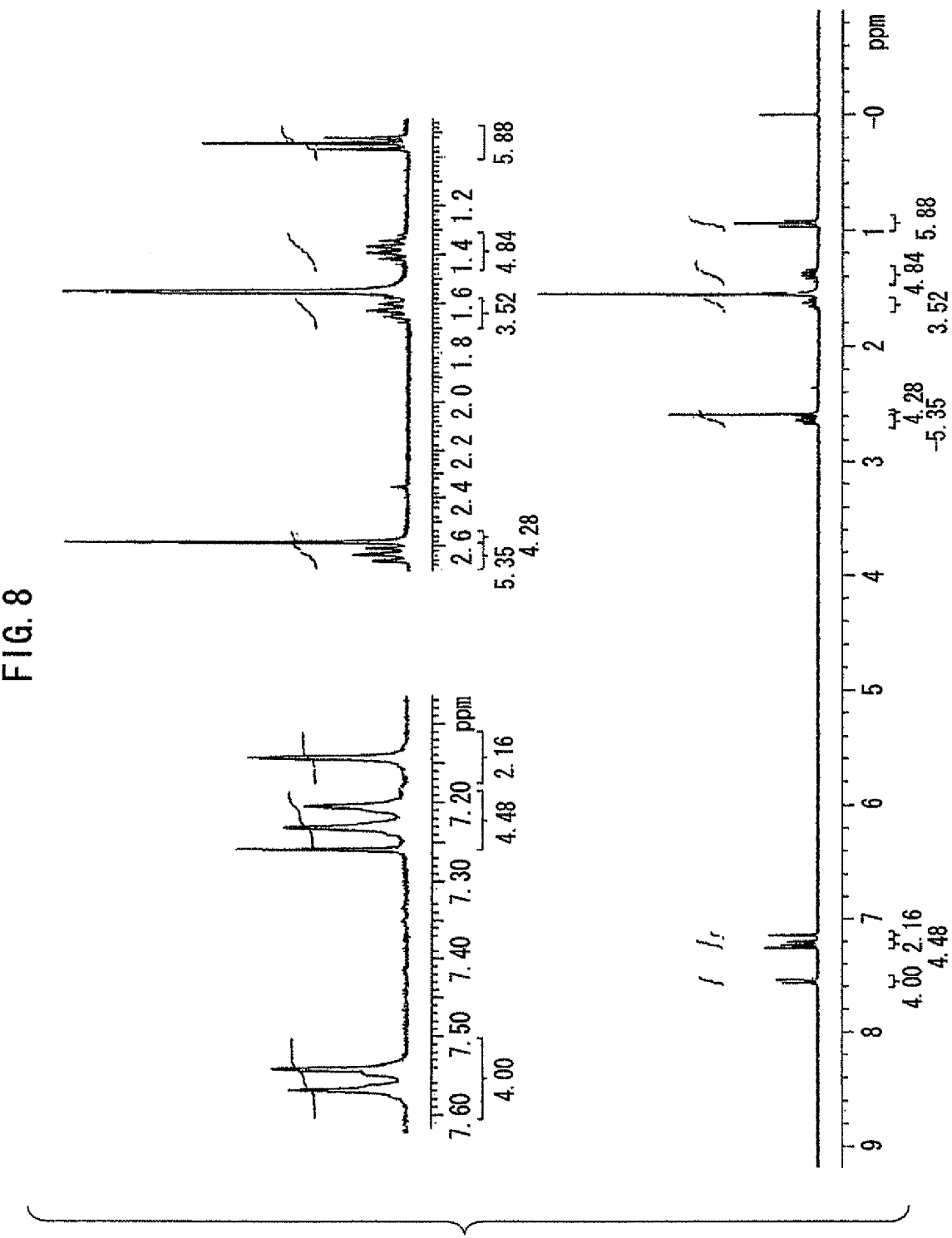
FIG. 8 shows a $^1$H-NMR spectrum in Example 4.

The IR spectrum and ¹H-NMR spectrum of the obtained Exemplary Compound 7 are shown in FIGS. 7 and 8, respectively.

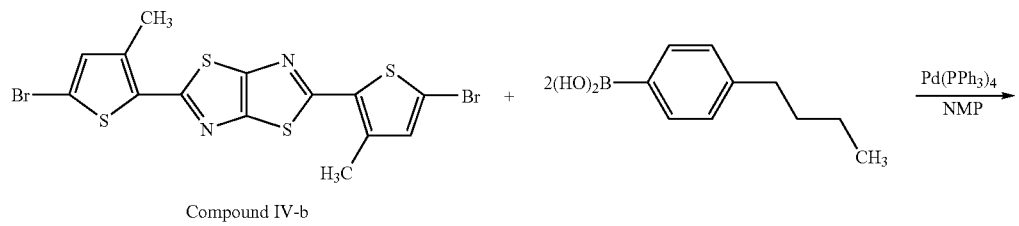

Compound IV-b

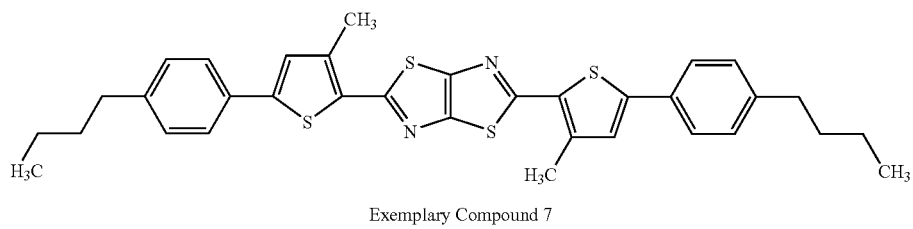

Exemplary Compound 7

Example 5

Under nitrogen atmosphere, 10 ml of a solution of 1.6M n-butyl lithium (16 mmol) in hexane is put into a 100 ml three-necked flask cooled at −80° C. After cooling to −80° C., 10 ml of THF is added dropwise thereto using a dropping funnel while the THF is maintained at −60° C. Thereafter, 3.1 g (16 mmol) of 1-bromo-4-n-octylbenzene maintained at −60° C. is added dropwise thereto using a dropping funnel. The resultant mixture is stirred at −40° C. for 1 hour, and a solution of 2.3 g (22 mmol) of trimethyl borate in 10 ml of THF is added dropwise to the mixture using a dropping funnel while the temperature of the added solution is maintained at −40° C. Thereafter, the temperature of the mixture is gradually increased to 10° C. over 2 hours, and 50 ml of a 10% HCl aqueous solution is added thereto at 0° C., and extraction is performed using 100 ml of toluene. The extract is washed with 100 ml of pure water three times, and is dehydrated using sodium sulfate. Toluene is distilled off by reducing the pressure, whereby remaining matter in an amount of 3.3 g is obtained. The remaining matter is washed with a mixed solution of 100 ml pure water/100 ml hexane, whereby 2.0 g of Compound V-a, which is 4-n-octylphenyl borate, is obtained. The obtained compound is identified as the desired product by $^1$H-NMR and IR.

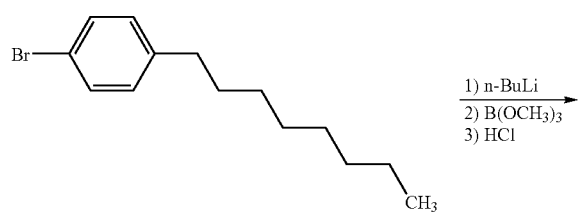

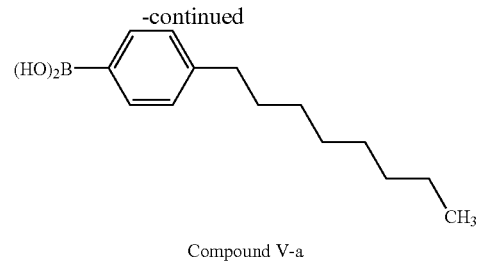

Compound V-a

Synthesis of Exemplary Compound 4

Under nitrogen atmosphere, 0.1 g (0.10 mmol) of tetrakistriphenylphosphine palladium(0) is dissolved in 100 ml of NMP in a 300 ml three-necked flask, 1.4 g (3.0 mmol) of Compound IV-a, 9.0 ml of a 2M sodium carbonate aqueous solution, and 1.4 g (6.0 mmol) of 4-n-octylphenyl borate (Compound V-a) are sequentially added, in this order, to the solution in the flask. The resultant mixture is refluxed for 5 hours in an oil bath at 200° C. under stirring by a magnetic stirrer. After the completion of the reaction is confirmed by $^1$H-NMR, the reaction solution is cooled to 25° C., and the reaction solution is poured into 1 L of pure water in a 2 L beaker. The resultant mixture in the beaker is stirred at 25° C. for 20 minutes using a magnetic stirrer After the completion of the stirring, the precipitated crystal is collected by suction filtration, and washed with 300 ml of pure water. The obtained crystal is further washed with 200 ml of methanol, and then with 100 ml of toluene, and vacuum-dried at 60° C. for 15 hours. The crystal is recrystallized using 200 ml of NMP, followed by purification by sublimation, whereby 0.60 g of Exemplary Compound 4 in the form of an orange crystal is obtained.

Figure 9:
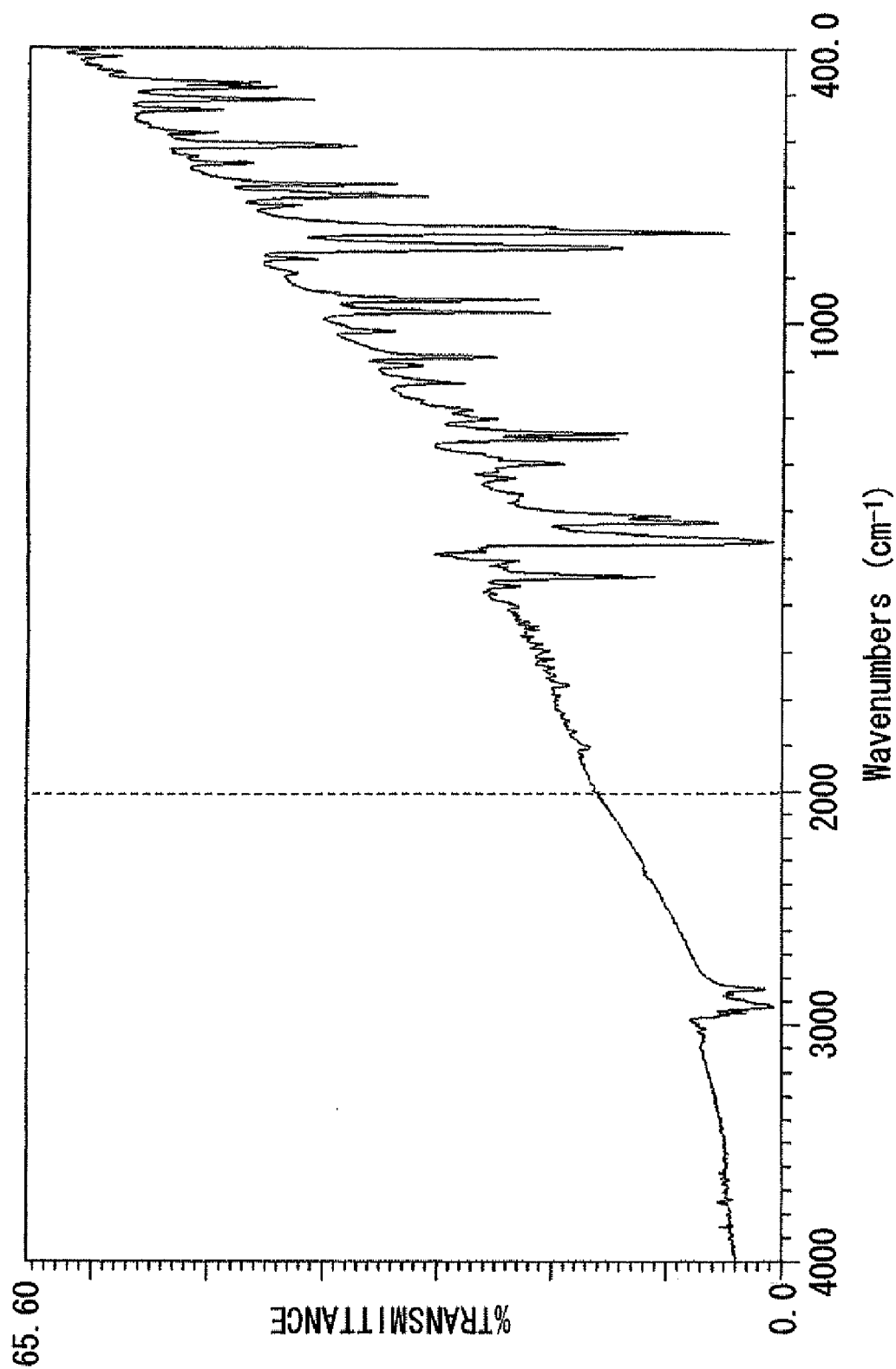
FIG. 9 shows an infrared absorption spectrum in Example 5.
Figure 10:
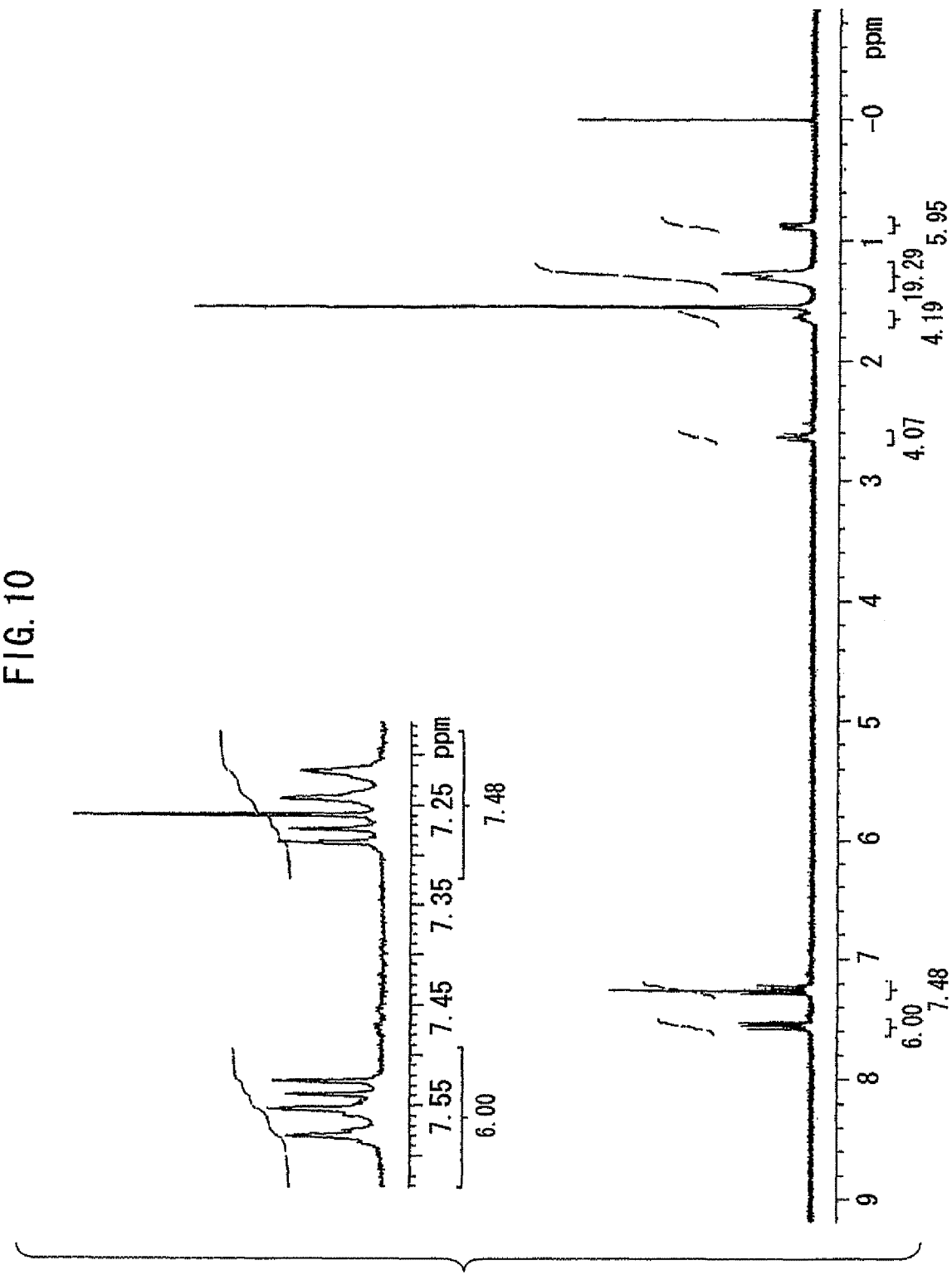
FIG. 10 shows a $^1$H-NMR spectrum in Example 5.

The IR spectrum and $^1$H-NMR spectrum of the obtained Exemplary Compound 4 are shown in FIGS. 9 and 10, respectively.

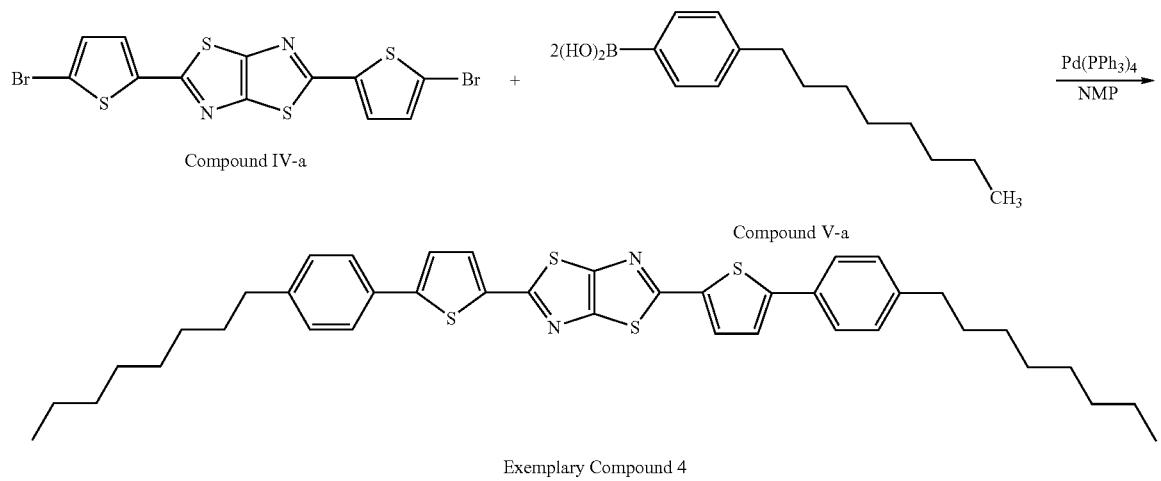

Compound IV-a

Compound V-a

Exemplary Compound 4

Example 6

Under nitrogen atmosphere, 20 ml of a solution of 1.6M n-butyl lithium (32 mmol) in hexane is put into a 200 ml three-necked flask cooled at −80° C. After cooling to −80° C., 20 ml of THF is added dropwise thereto using a dropping funnel while the THF is maintained at −60° C. Thereafter, 10 g (32 mmol) of 1-bromo-4-n-dodecylbenzene maintained at −60° C. is added dropwise thereto using a dropping funnel. The resultant mixture is stirred at −40° C. for 1 hour, and a solution of 4.5 g (43 mmol) of trimethyl borate in 10 ml of THF is added to the mixture using a dropping funnel while the temperature of the added solution is maintained at −40° C. Thereafter, the temperature of the mixture is gradually increased to 10° C. over 2 hours, and 50 ml of a 10% HCl aqueous solution is added thereto at 0° C., and extraction is performed using 100 ml of toluene. The extract is washed with 100 ml of pure water three times, and is dehydrated using sodium sulfate. Toluene is distilled off by reducing the pressure, whereby remaining matter is obtained. The remaining matter is washed with a mixed solution of 100 ml pure water/ 100 ml hexane, whereby 1.8 g of Compound V-b, which is 4-n-dodecylphenyl borate, is obtained. The obtained compound is identified as the desired product by $^1$H-NMR and IR.

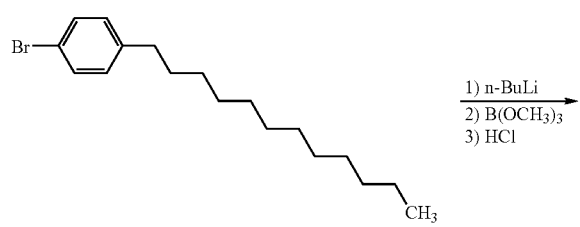

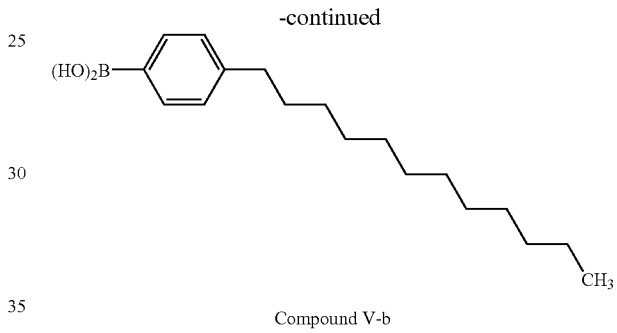

Compound V-b

Under nitrogen atmosphere, 0.10 g (0.080 mmol) of tetrakistriphenylphosphine palladium(0) is dissolved in 100 ml of NMP in a 300 ml three-necked flask. 1.2 g (2.5 mmol) of Compound IV-a, 6.0 ml of a 2M sodium carbonate aqueous solution, and 1.5 g (5.0 mmol) of Compound V-b, which is 4-n-dodecylphenyl borate, are sequentially added, in this order, to the solution in the flask. The resultant mixture is refluxed for 5 hours in an oil bath at 220° C. under stirring by a magnetic stirrer. After the completion of the reaction is confirmed by $^1$H-NMR, the reaction solution is cooled to 25° C., and the reaction solution is poured into 400 ml of pure water in a 1 L beaker. The resultant mixture in the beaker is stirred at 25° C. for 30 minutes using a magnetic stirrer After the completion of the stirring, the precipitated crystal is collected by suction filtration, and washed with 300 ml of pure water. The obtained crystal is further washed with 200 ml of methanol, and then with 100 ml of toluene, and vacuum-dried at 60° C. for 15 hours. The crystal is recrystallized twice from 200 ml of NMP, followed by purification by sublimation, whereby 0.13 g of Exemplary Compound 5 in the form of an orange crystal is obtained.

Figure 11:
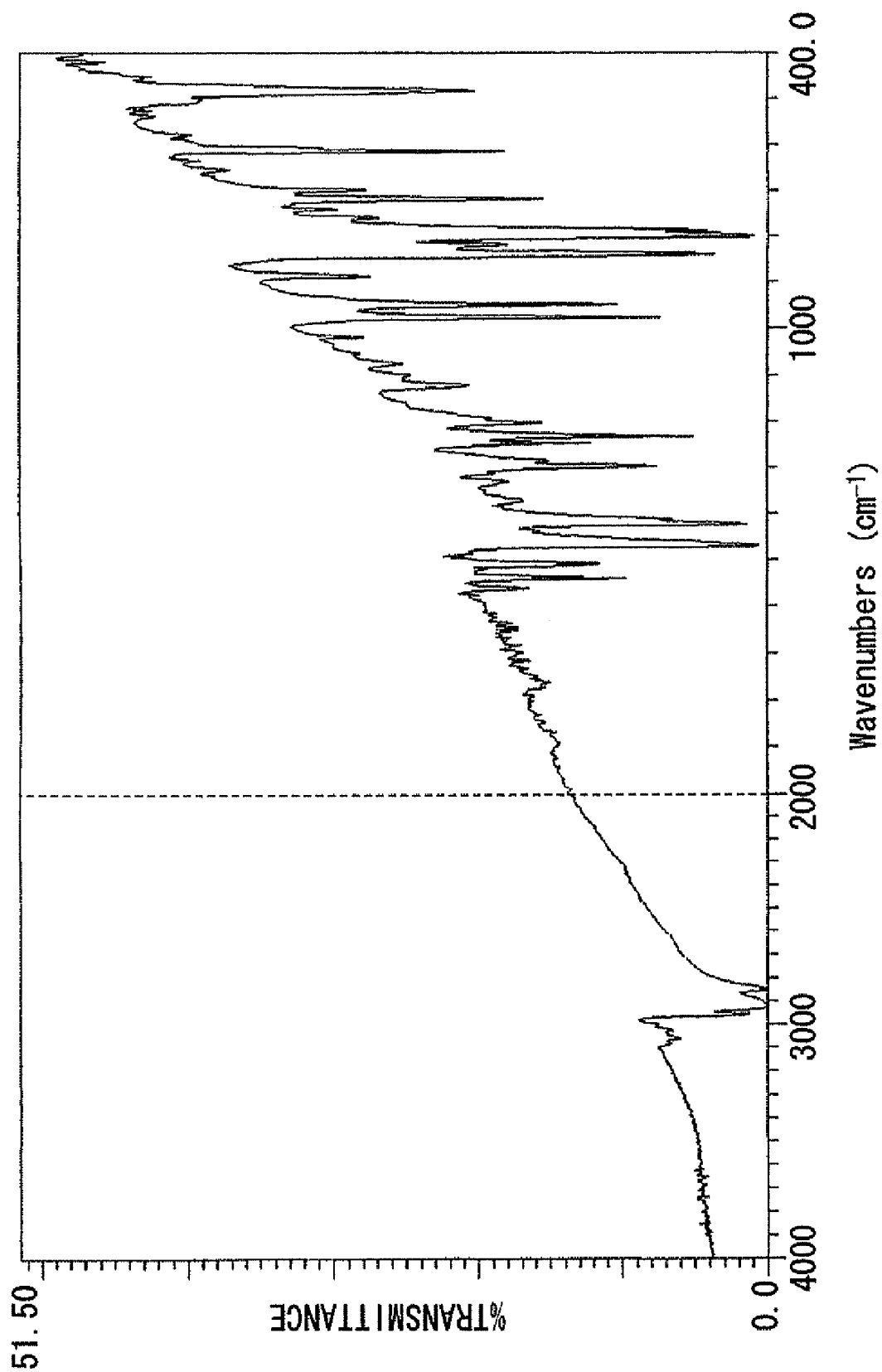
FIG. 11 shows an infrared absorption spectrum in Example 6.
Figure 12:
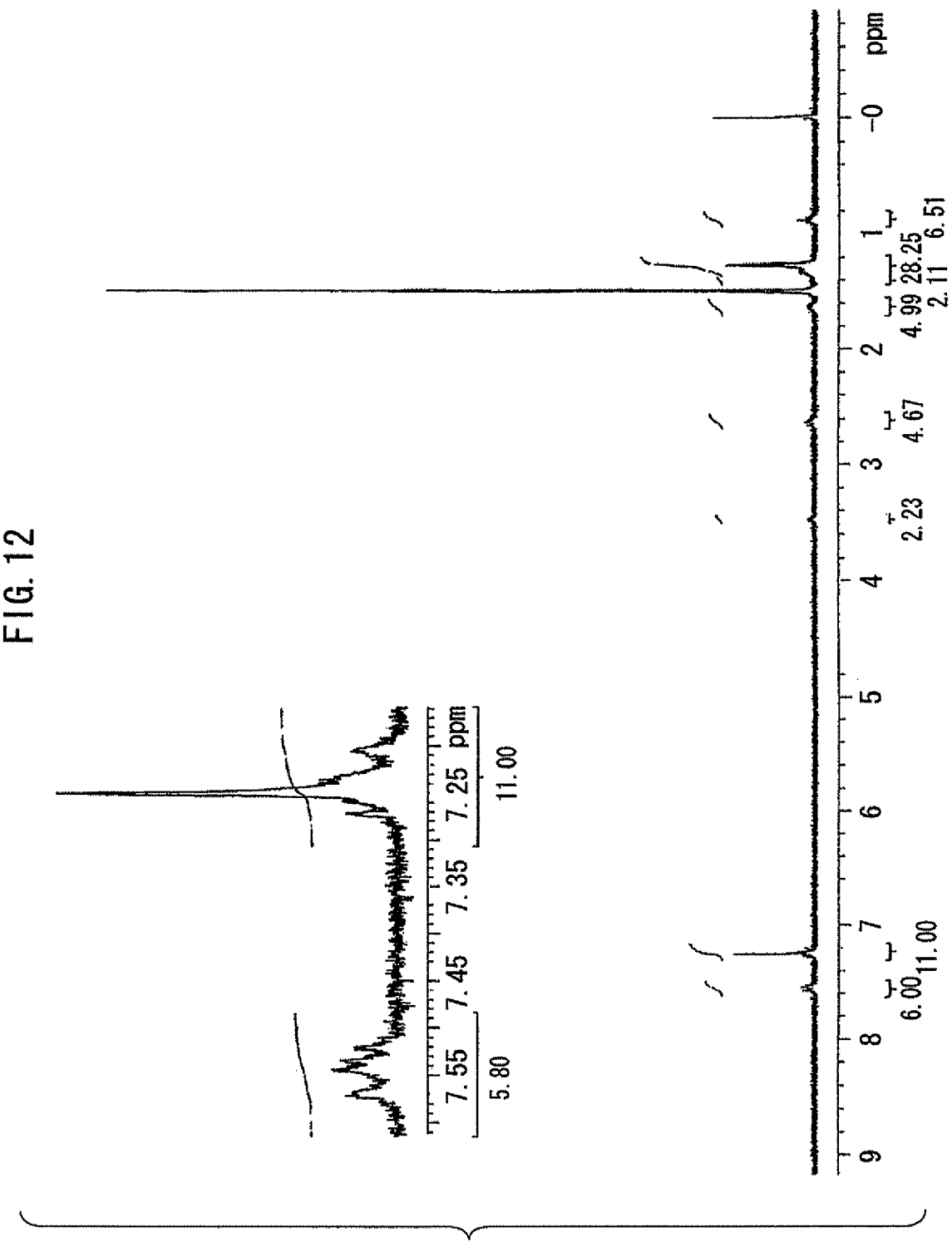
FIG. 12 shows a $^1$H-NMR spectrum in Example 6.

The IR spectrum (according to the KBr method) of the obtained Exemplary Compound 5 is shown in FIG. 11. The NMR spectrum (H-NMR, solvent: CDCl$_3$) thereof is shown in FIG. 12.

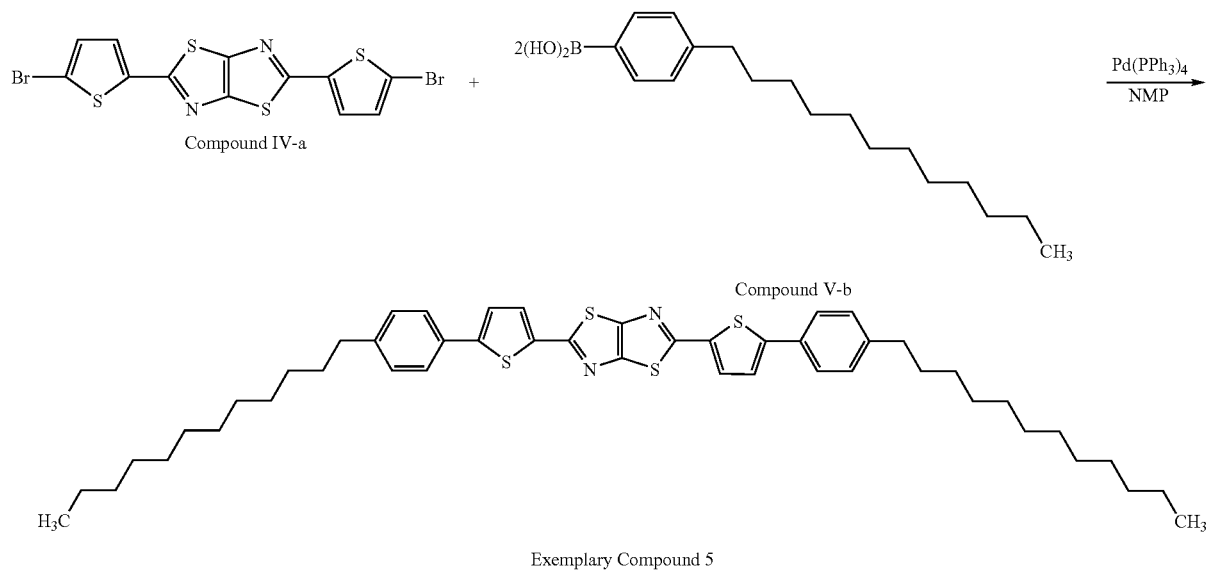

Exemplary Compound 5

Example 7

Synthesis of Compound VI-a 60 g (305 mmol) of 3-n-octylthiophene is dissolved in 100 ml of DMF in a 500 ml four-necked flask. The resultant solution is cooled to 5° C., and a solution obtained by dissolving 55 g (310 mmol) of NBS in 50 ml of DMF is added dropwise thereto over 5 minutes using a pressure equalizing funnel. Thereafter, the resultant solution is stirred at 25° C. for 1 hour using a magnetic stirrer, and then added into 500 ml of pure water in a 1 L beaker. The resultant mixture in the beaker is stirred at 25° C. for 20 minutes using a magnetic stirrer. 300 ml of ethyl acetate is added to the solution in the beaker, and the contents of the beaker are stirred at 25° C. for 10 minutes using a magnetic stirrer. The ethyl acetate layer is taken out, washed with 300 ml of pure water three times, and dehydrated using anhydrous sodium sulfate. Then, the resultant liquid is subjected to filtration, and solvent is removed by distillation under reduced pressure, whereby 83 g of a yellow oily material is obtained. The yellow oily material is subjected to vacuum distillation (at 1 mmHg to 3 mmHg and a temperature of 120 to 130° C.), whereby 76 g of a pale-yellow oily material is obtained (yield: 93%).

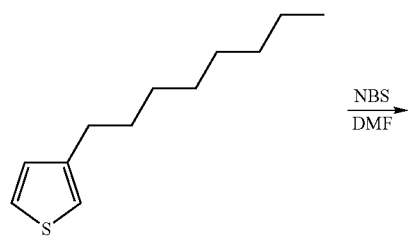

-continued

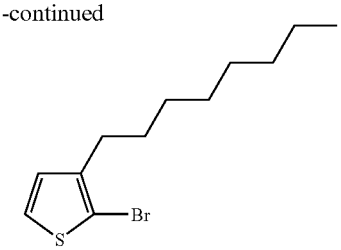

Compound VI-a

Synthesis of Compound VI-b

A 500 ml four-necked flask is sufficiently dried, and 9.1 g (374 mmol) of magnesium and 100 ml of THF are added into the flask under nitrogen atmosphere. Three particles of particulate iodine are added into the flask, thereby activating the surface of the magnesium. Thereafter, the contents of the flask are heated to 60° C., and a solution of 100 g (363 mmol) of Compound VI-a in 50 ml of THF is added dropwise into the flask as the reaction in the flask proceeds. After completion of the dropwise addition, the contents of the flask are refluxed and stirred until the magnesium is completely consumed, and are cooled to 40° C. 30 ml of DMF, which has been dehydrated using calcium hydride, is added dropwise into the obtained solution over 10 minutes, and then the contents of the flask are heated at 50° C. for 30 minutes while stirring with a magnetic stirrer. After completion of the reaction, the contents in the flask are cooled to 5° C., and are poured into a 1 L beaker containing 400 ml of 10% hydrochloric acid and 300 ml of toluene. The contents of the beaker are stirred at 25° C. for 30 minutes using a magnetic stirrer, and the toluene layer is taken out and washed with 300 ml of pure water three times. Thereafter, the resultant liquid is dehydrated with anhydrous sodium sulfate and then filtrated, and solvent is removed by distillation under reduced pressure, whereby 94 g of a red oily material is obtained. The red oily material is subjected to vacuum distillation (at 1 mmHg to 3 mmHg and a temperature of 140 to 150° C.), whereby 52 g of a yellow oily material is obtained (yield: 64%). The obtained compound is identified as the desired product by ¹H-NMR and IR.

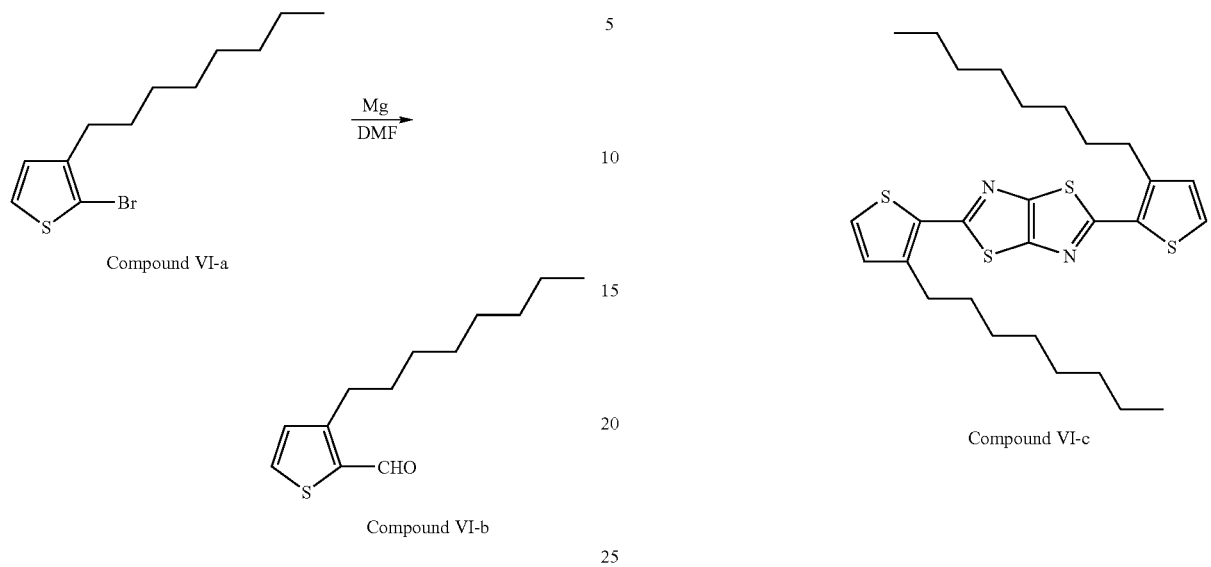

Synthesis of Compound VI-c 8.0 g (67 mmol) of rubeanic acid and 60 g (267 mmol) of Compound VI-b are added into a 300 ml four-necked flask, and dissolved in 60 ml of dimethylformamide. The resultant solution is stirred at 150° C. for 4 hours using a magnetic stirrer, and is cooled to 25° C. The reaction solution is added into 300 ml of pure water in a 1 L beaker, and the contents of the beaker are stirred at 25° C. for 30 minutes using a magnetic stirrer. 300 ml of toluene is added into the beaker, and the contents of the beaker are stirred for 10 minutes using a magnetic stirrer. The toluene layer is taken out, washed with 300 ml of pure water three times, and dehydrated using anhydrous sodium sulfate. Then, the resultant liquid is subjected to filtration, and solvent is removed by distillation under reduced pressure, whereby a brown oily material is obtained. 200 ml of methanol is added to the brown oily material, and the raw materials are removed therefrom by decantation, 200 ml of hexane is added to the remaining matter, and cooled to 5° C., thereby causing crystallization. The obtained crystal is collected by suction filtration, and the collected material is washed by pouring 100 ml of methanol, whereby 12 g of an orange crystal is obtained (yield: 38%). The obtained compound is identified as the desired product by ¹H-NMR and IR.

Synthesis of Compound VI-d

Under nitrogen atmosphere, 12 g (23 mmol) of Compound VI-c and 8.9 g (50 mmol) of NBS are placed in a 500 ml three-necked flask, and are dissolved in 200 ml of DMF. The contents of the flask are stirred at 40° C. for 1 hour using a magnetic stirrer, thereby completing the reaction. The reaction solution is cooled to 25° C., and is added into 500 ml of pure water in a 2 L beaker. The contents of the beaker are stirred at 5° C. for 30 minutes using a magnetic stirrer. After completion of the stirring, the precipitate crystal is collected by suction filtration, and is washed with 1 L of pure water. The crystal is further washed with 100 ml of methanol, and is vacuum-dried at 60° C. for 15 hours, whereby 12.2 g of an orange crystal is obtained (yield: 76%). The obtained compound is identified as the desired product by ¹H-NMR and IR.

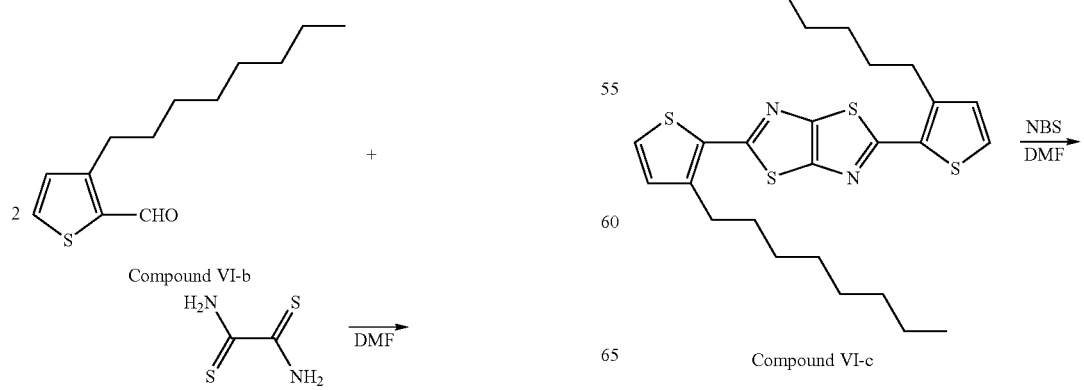

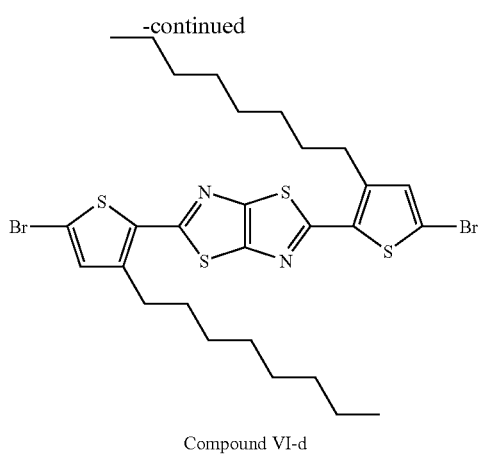

Compound VI-d

Synthesis of Exemplary Compound 25

Under nitrogen atmosphere, 0.10 g (0.090 mmol) of tetrakistriphenylphosphine palladium (0) is dissolved in 60 ml of THF in a 200 ml three-necked flask. 2.06 g (3.0 mmol) of Compound VI-d, 7.0 ml of a 2M aqueous sodium carbonate solution, and 1.18 g (6.6 mmol) of 4-n-butylphenyl borate are added, in this order, to the solution in the flask. The resultant mixture is refluxed for 8 hours under stirring by a magnetic stirrer. After the completion of the reaction is confirmed by $^1$H-NMR, the reaction solution is cooled to 25° C., and the reaction solution is poured into a 1 L beaker containing 80 ml of a 5% aqueous hydrochloric acid solution and 200 ml of toluene. Then, the contents of the beaker are stirred at 25° C. for 30 minutes using a magnetic stirrer. The toluene layer is taken out, washed with 200 ml of pure water three times, and dehydrated using anhydrous sodium sulfate. Then, the liquid is filtrated, and solvent is removed by distillation under reduced pressure, whereby 2.8 g of a red oily material is obtained. The palladium is removed therefrom by using a silica gel permeation column, and the resulting substance is washed with 50 ml of methanol and 20 ml of hexane, and recrystallized using 100 ml of hexane. The obtained crystal is vacuum-dried for 15 hours, whereby 1.8 g of Exemplary Compound 25 in the form of an orange crystal is obtained (yield: 78%).

Figure 13:
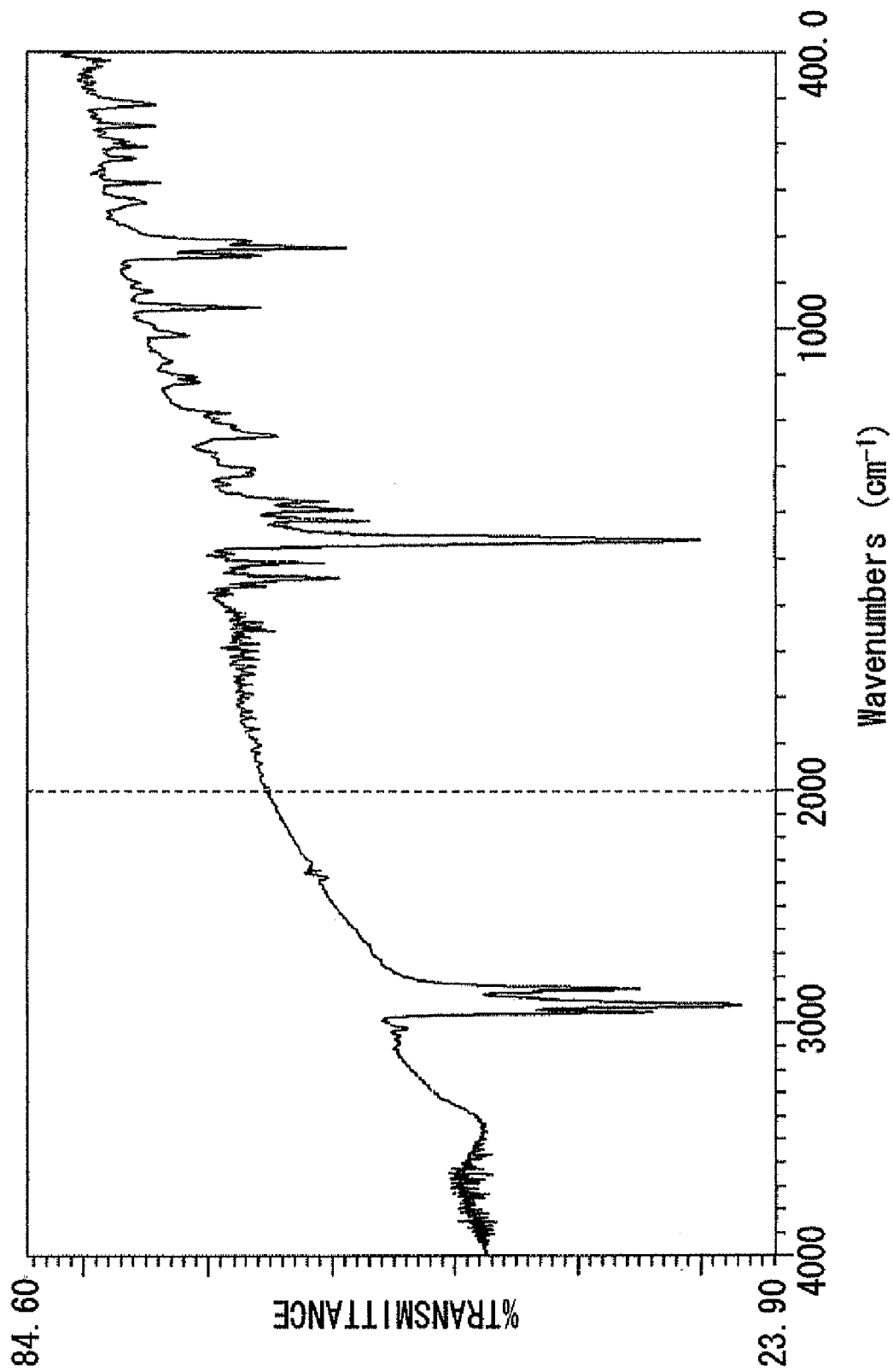
FIG. 13 shows an infrared absorption spectrum in Example 7.
Figure 14:
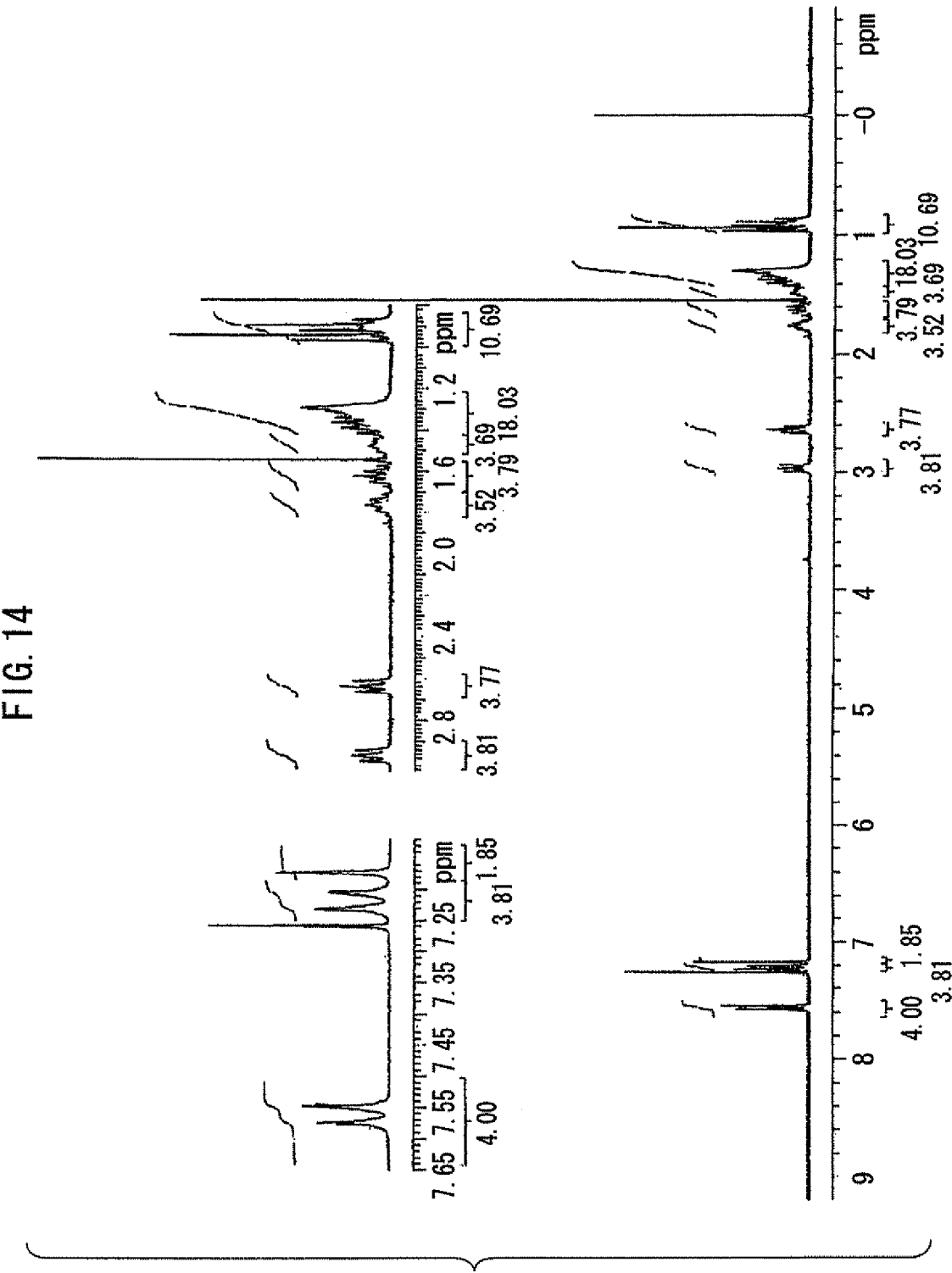
FIG. 14 shows a $^1$H-NMR spectrum in Example 7.

The IR spectrum (according to the KBr method) of the obtained Exemplary Compound 25 is shown in FIG. 13. The NMR spectrum ($^1$H-NMR, solvent: CDCl$_3$) thereof is shown in FIG. 14.

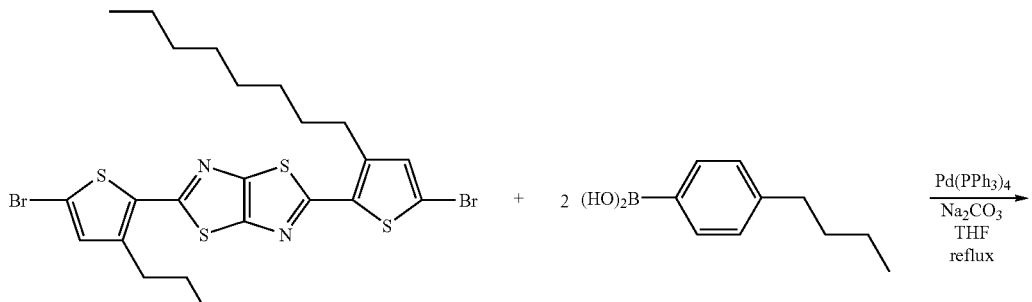

Compound VI-d

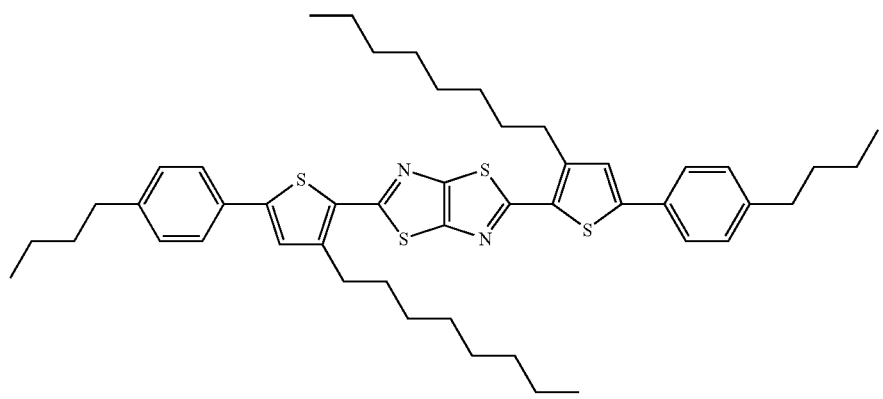

Exemplary Compound 25

Example 8

Synthesis of Exemplary Compound 27

Under nitrogen atmosphere, 0.090 g (0.080 mmol) of tetrakistriphenylphosphine palladium (0) is dissolved in 50 ml of THF in a 200 ml three-necked flask. 1.72 g (2.5 mmol) of Compound VI-d, 6.0 ml of a 2M aqueous sodium carbonate solution, and 1.23 g (5.3 mmol) of Compound V-a are added, in this order, to the solution in the flask. The resultant mixture is refluxed for 11 hours under stirring by a magnetic stirrer. After the completion of the reaction is confirmed by $^1$H-NMR, the reaction solution is cooled to 25° C., and the reaction solution is poured into a 1 L beaker containing 100 ml of a 5% aqueous hydrochloric acid solution and 200 ml of toluene. Then, the contents of the beaker are stirred at 25° C. for 30 minutes using a magnetic stirrer. The toluene layer is taken out, washed with 200 ml of pure water three times, and dehydrated using anhydrous sodium sulfate. Then, the liquid is filtrated, and solvent is removed by distillation under reduced pressure, whereby 2.8 g of a red solid material is obtained. The red solid material is subjected to purification by a silica gel column using a mixed solvent of toluene and hexane (in a mixing ratio by weight of 1:5), and recrystallized using a mixed solvent of ethanol and hexane (in a mixing ratio by weight of 1:1). The obtained crystal is vacuum-dried for 15 hours, whereby 0.7 g of Exemplary Compound 27 in the form of an orange crystal is obtained (yield: 30%).

Figure 15:
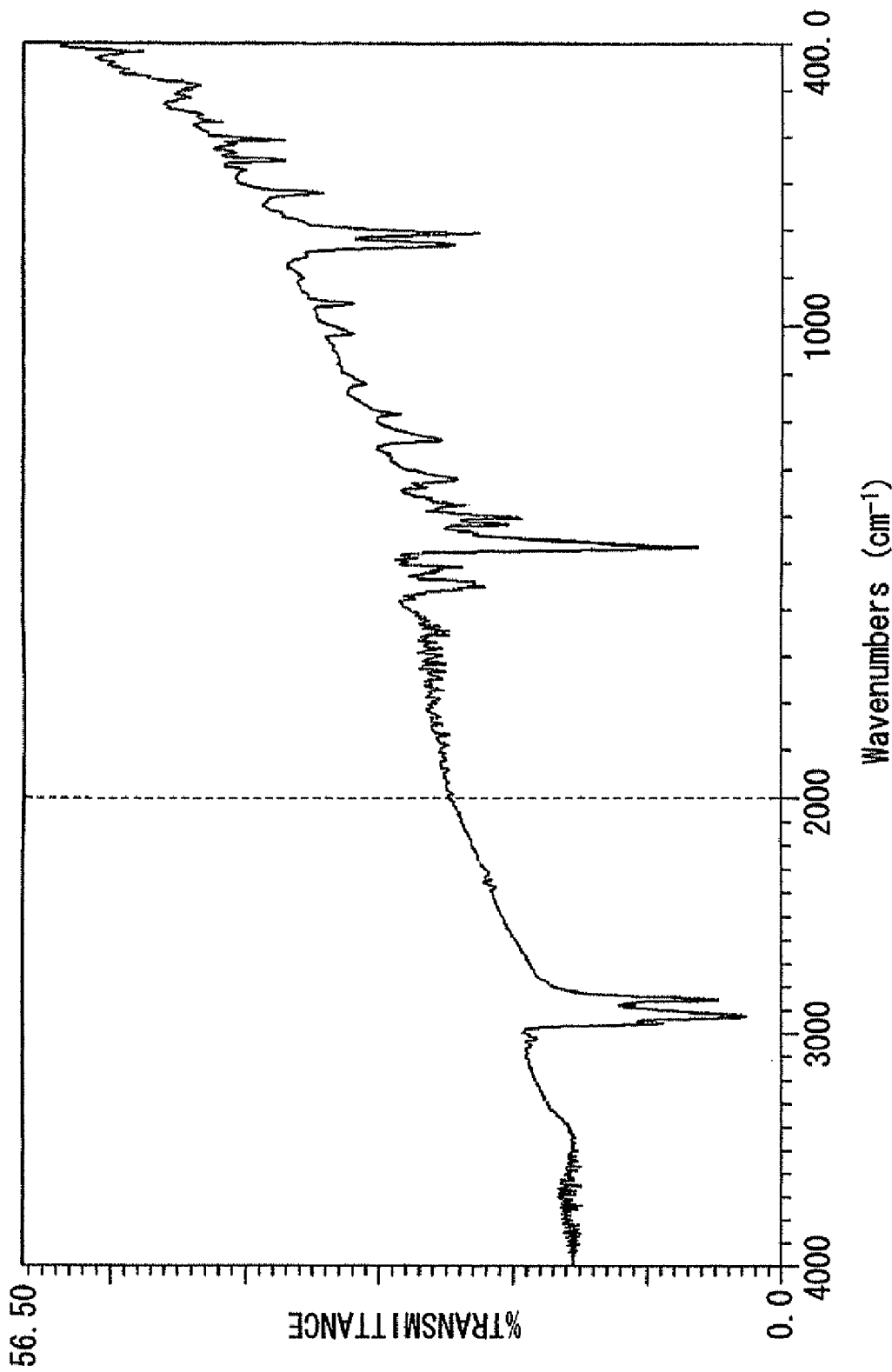
FIG. 15 shows an infrared absorption spectrum in Example 8.
Figure 16:
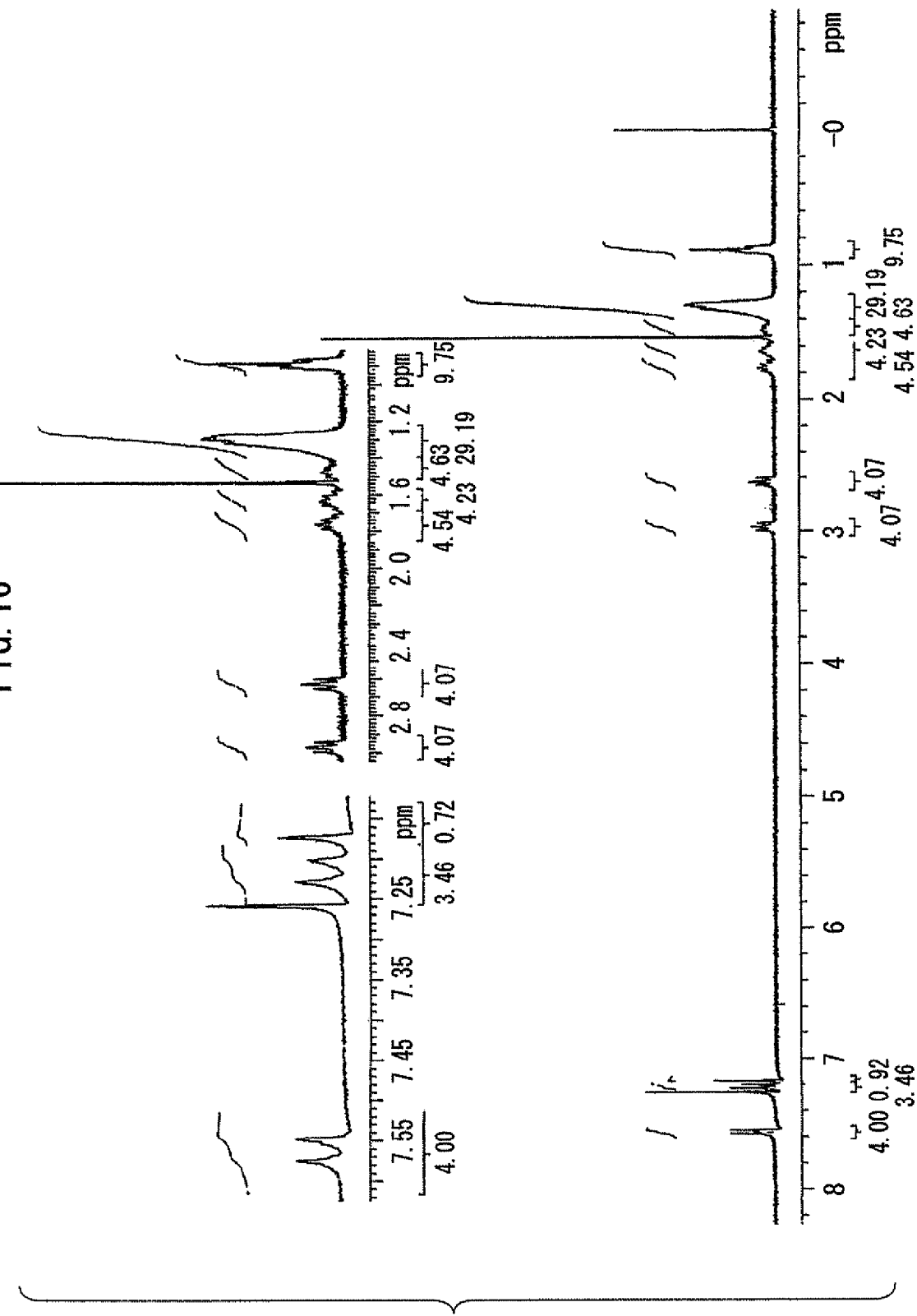
FIG. 16 shows a $^1$H-NMR spectrum in Example 8.

The IR spectrum (according to the KBr method) of the obtained Exemplary Compound 27 is shown in FIG. 15. The NMR spectrum ($^1$H-NMR, solvent: CDCl$_3$) thereof is shown in FIG. 16.

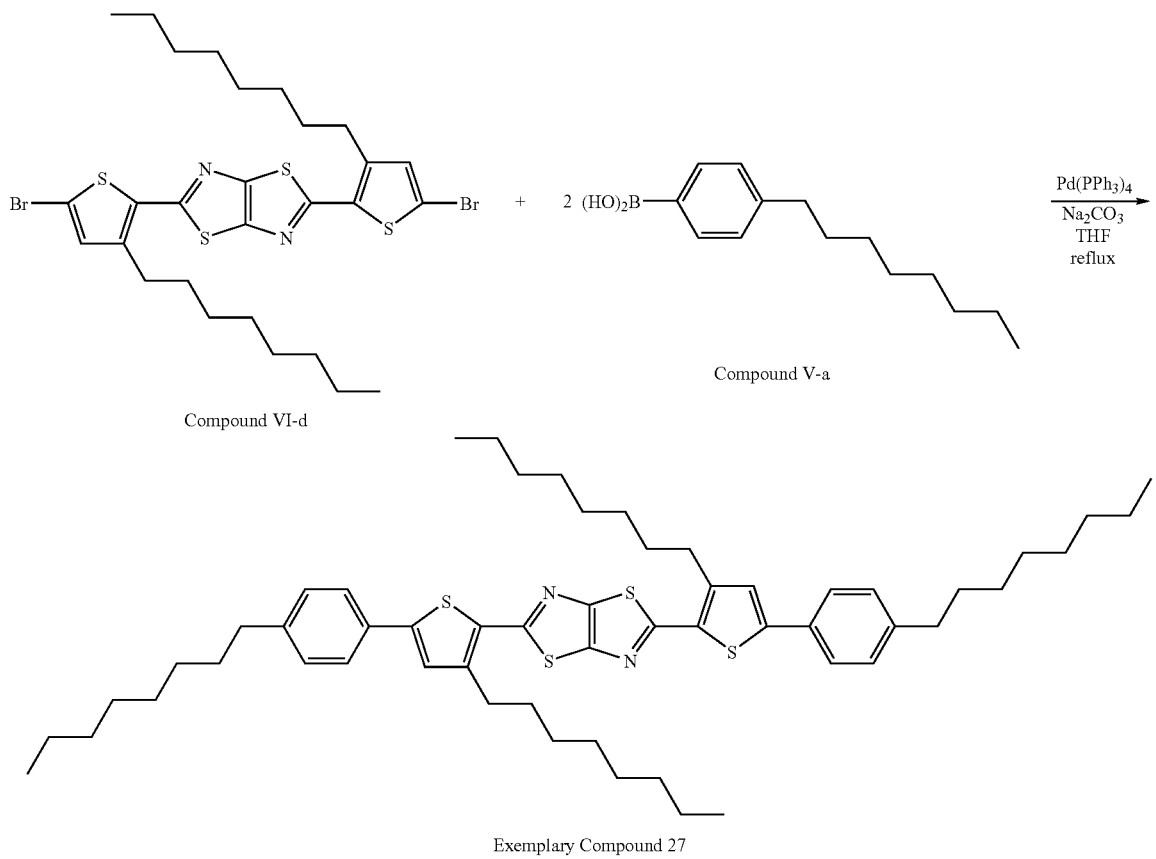

Compound VI-d

Compound V-a

Exemplary Compound 27

Example 9

Synthesis of Exemplary Compound 28

Under nitrogen atmosphere, 0.090 g (0.080 mmol) of tetrakistriphenylphosphine palladium (0) is dissolved in 50 ml of THF in a 200 ml three-necked flask, 1.72 g (2.5 mmol) of Compound VI-d, 6.0 ml of a 2M aqueous sodium carbonate solution, and 1.52 g (5.3 mmol) of Compound V-b are added, in this order, to the solution in the flask. The resultant mixture is refluxed for 12 hours under stirring by a magnetic stirrer. After the completion of the reaction is confirmed by $^1$H-NMR, the reaction solution is cooled to 25° C., and the reaction solution is poured into a 1 L beaker containing 100 ml of a 5% aqueous hydrochloric acid solution and 200 ml of toluene. Then, the contents of the beaker are stirred at 25° C. for 30 minutes using a magnetic stirrer. The toluene layer is taken out, washed with 200 ml of pure water three times, and dehydrated using anhydrous sodium sulfate. Then, the liquid is filtrated, and solvent is removed by distillation under reduced pressure, whereby 3.1 g of an orange solid material is obtained. The orange solid material is subjected to purification by a silica gel column using a mixed solvent of toluene and hexane, and recrystallized using a mixed solvent of ethanol and hexane. The obtained crystal is vacuum-dried for 15 hours, whereby 1.2 g of Exemplary Compound 28 in the form of an orange crystal is obtained (yield: 47%).

Figure 17:
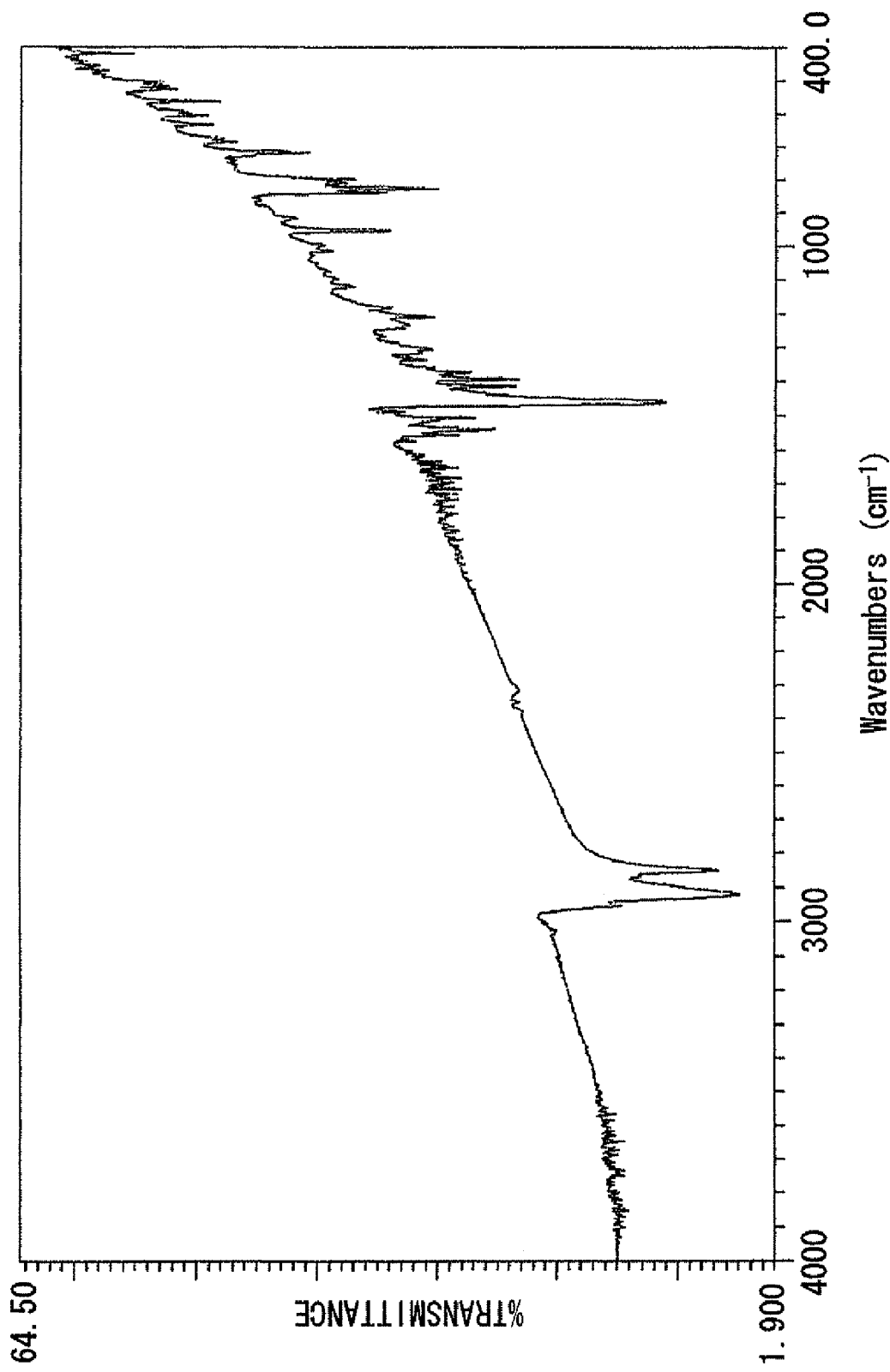
FIG. 17 shows an infrared absorption spectrum in Example 9.
Figure 18:
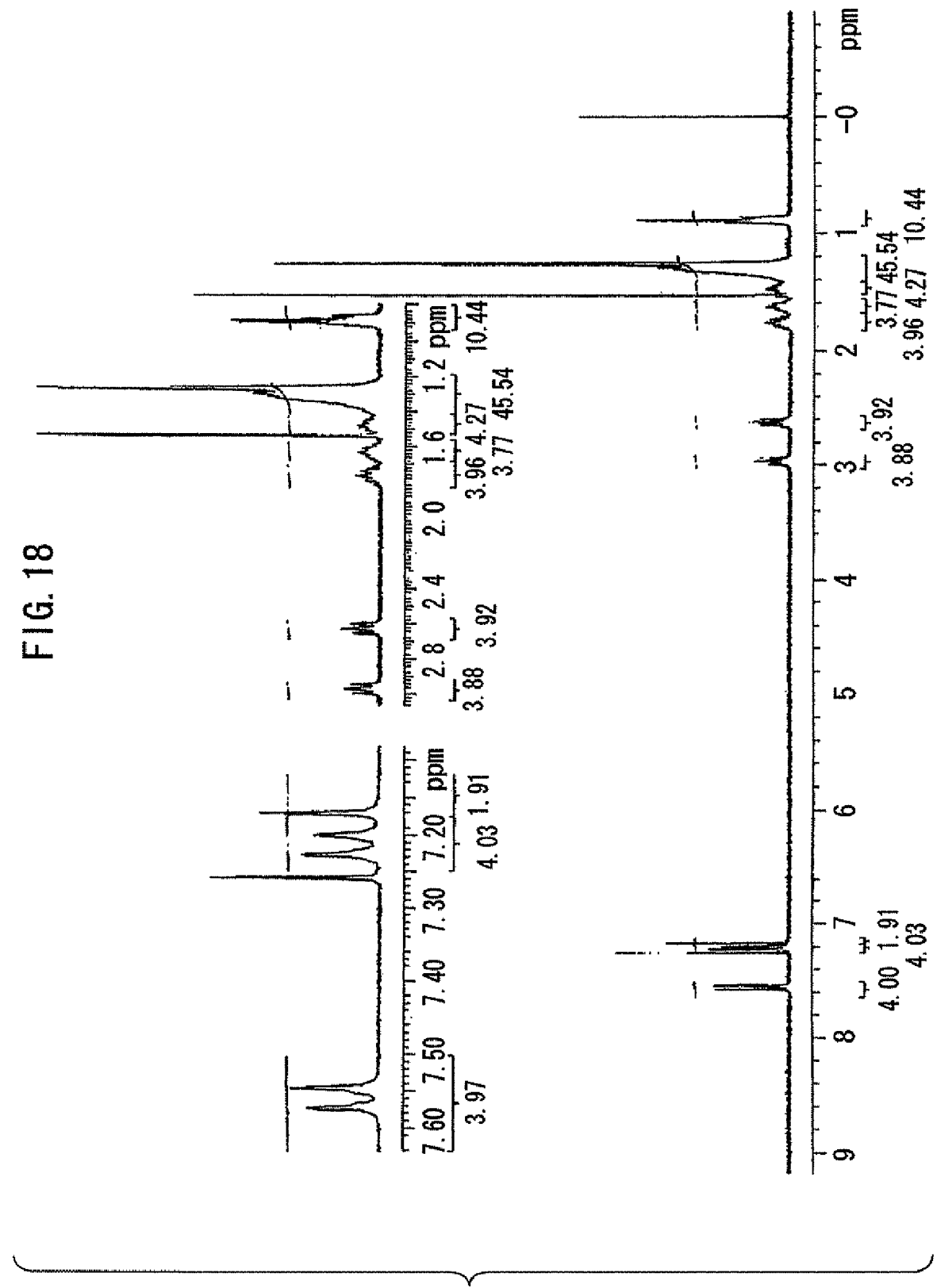
FIG. 18 shows a $^1$H-NMR spectrum in Example 9.

The IR spectrum (according to the KBr method) of the obtained Exemplary Compound 28 is shown in FIG. 17. The NMR spectrum ($^1$H-NMR, solvent: CDCl$_3$) thereof is shown in FIG. 18.

After the completion of the reaction is confirmed by $^1$H-NMR, the reaction solution is cooled to 25° C., and the reaction solution is poured into a 1 L beaker containing 100 ml of a 5% aqueous hydrochloric acid solution and 200 ml of toluene. Then, the contents of the beaker are stirred at 25° C. for 30 minutes using a magnetic stirrer. The toluene layer is taken out, washed with 200 ml of pure water three times, and dehydrated using anhydrous sodium sulfate. Then, the liquid

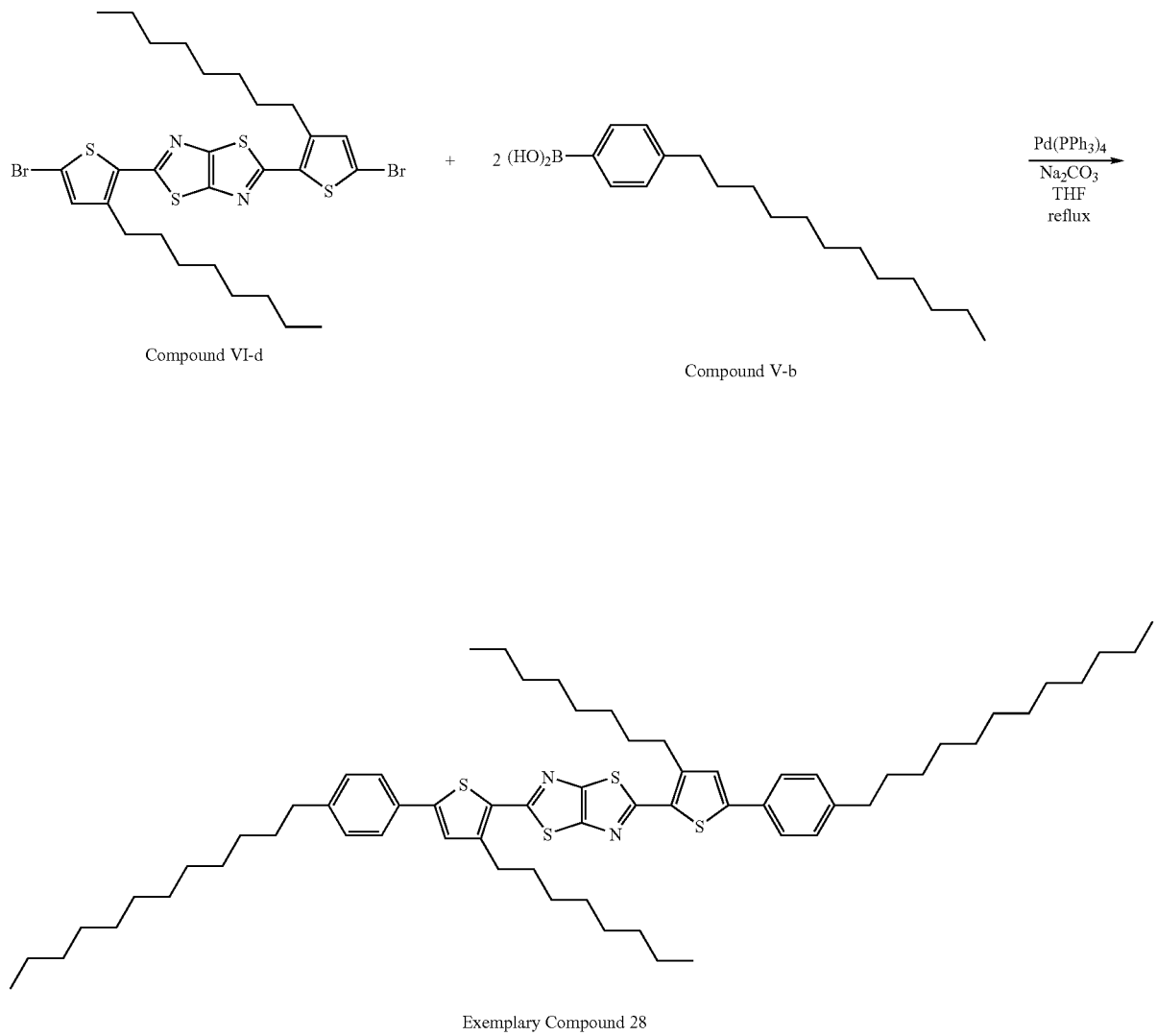

Exemplary Compound 28

Example 10

Synthesis of Exemplary Compound 8

Under nitrogen atmosphere, 0.090 g (0.080 mmol) of tetrakistriphenylphosphine palladium (0) is dissolved in 50 ml of THF in a 200 ml three-necked flask. 1.23 g (2.5 mmol) of Compound IV-b, 6.0 ml of a 2M aqueous sodium carbonate solution, and 1.24 g (5.3 mmol) of Compound V-a are added, in this order, to the solution in the flask. The resultant mixture is refluxed for 12 hours under stirring by a magnetic stirrer.

is filtrated, and solvent is removed by distillation under reduced pressure, whereby 1.7 g of an orange solid material is obtained. The orange solid material is subjected to purification by a silica gel column using a mixed solvent of toluene and THF (in a mixing ratio by weight of 1:2), and recrystallized using toluene. The obtained crystal is vacuum-dried for 15 hours, whereby 1.2 g of Exemplary Compound 8 in the form of an orange crystal is obtained (yield: 70%).

Figure 19:
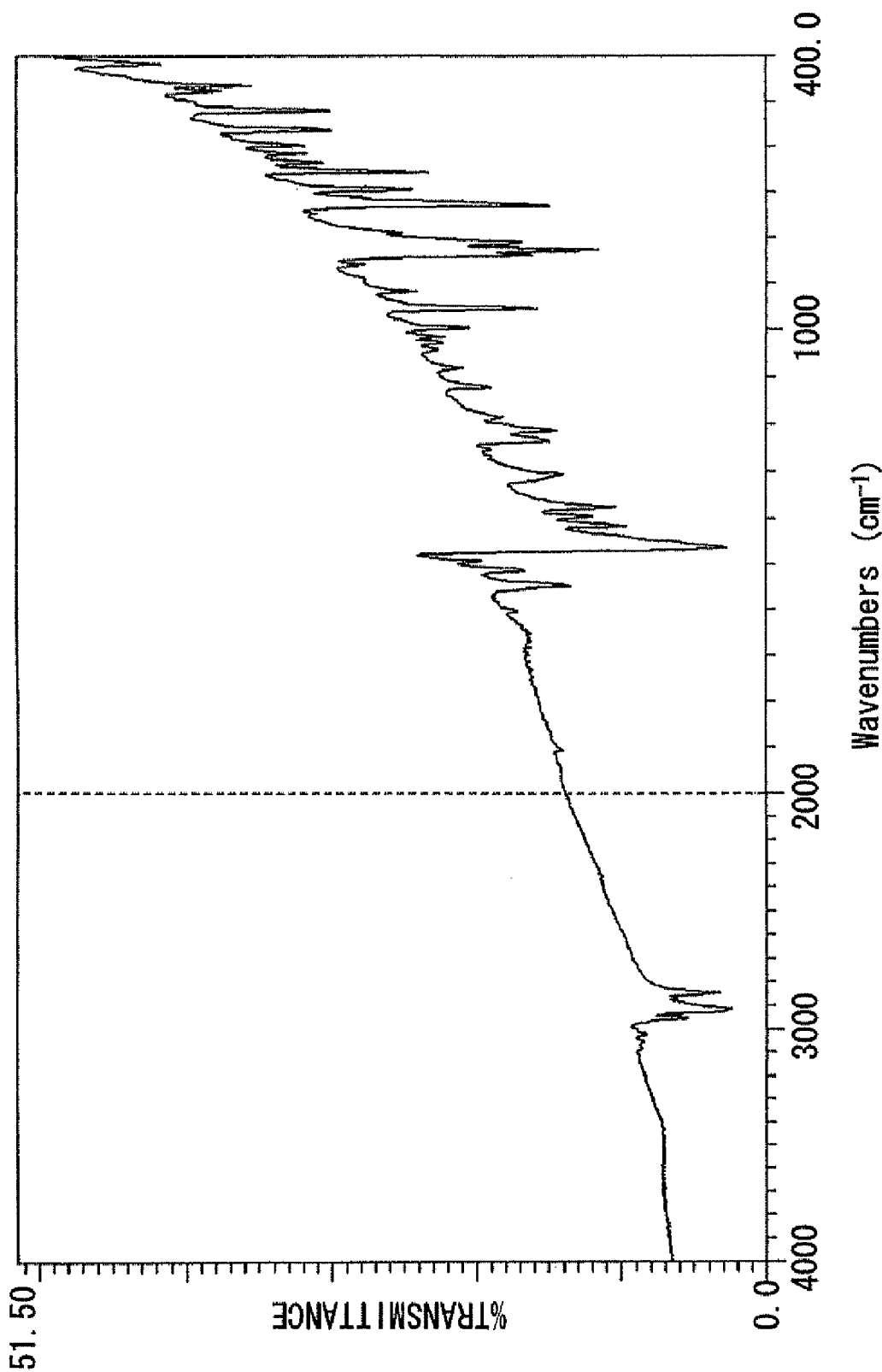
FIG. 19 shows an infrared absorption spectrum in Example 10.
Figure 20:
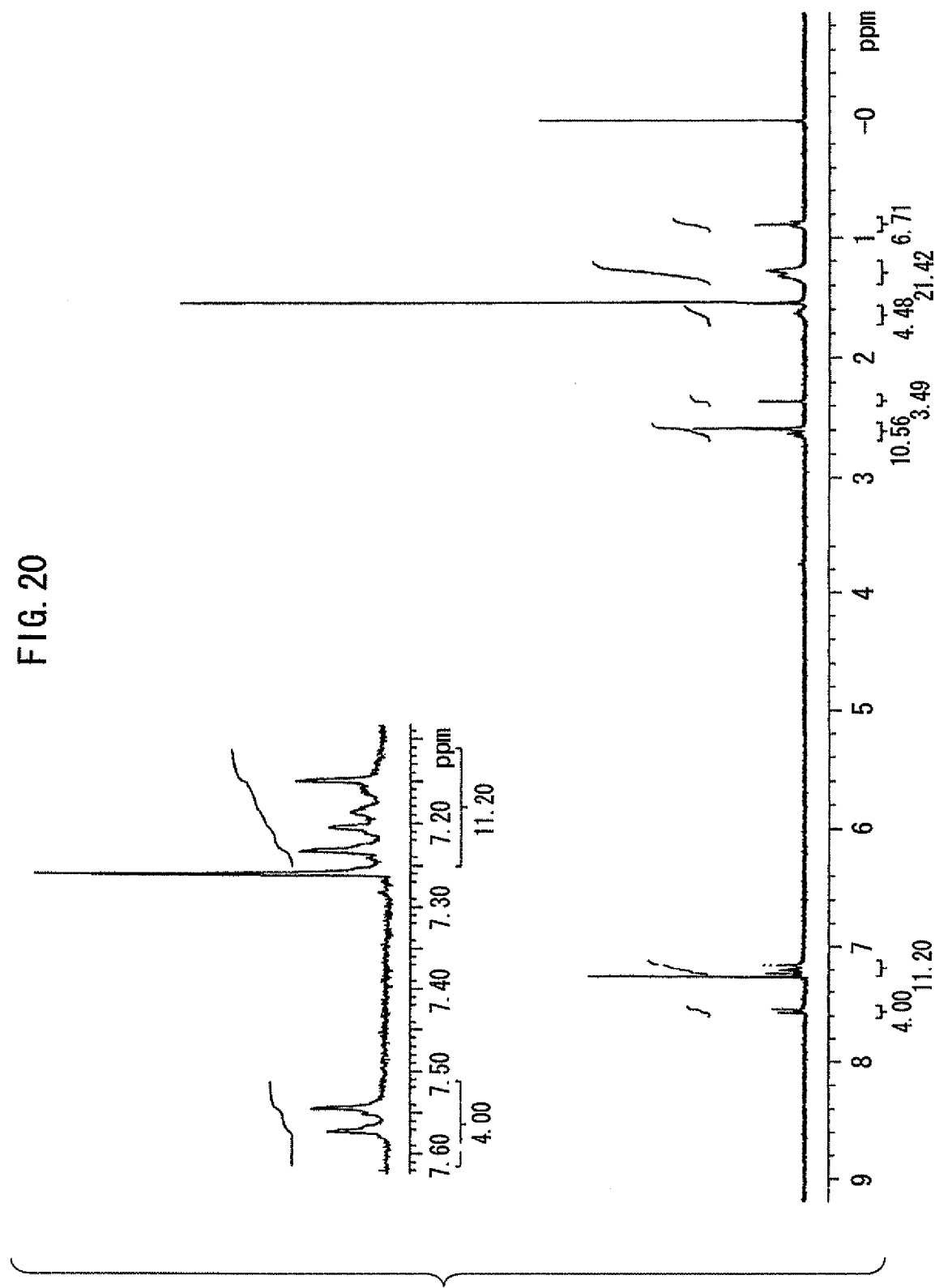
FIG. 20 shows a $^1$H-NMR spectrum in Example 10.

The IR spectrum (according to the KBr method) of the obtained Exemplary Compound 8 is shown in FIG. 19. The NMR spectrum ($^1$H-NMR, solvent: CDCl$_3$) thereof is shown in FIG. 20.

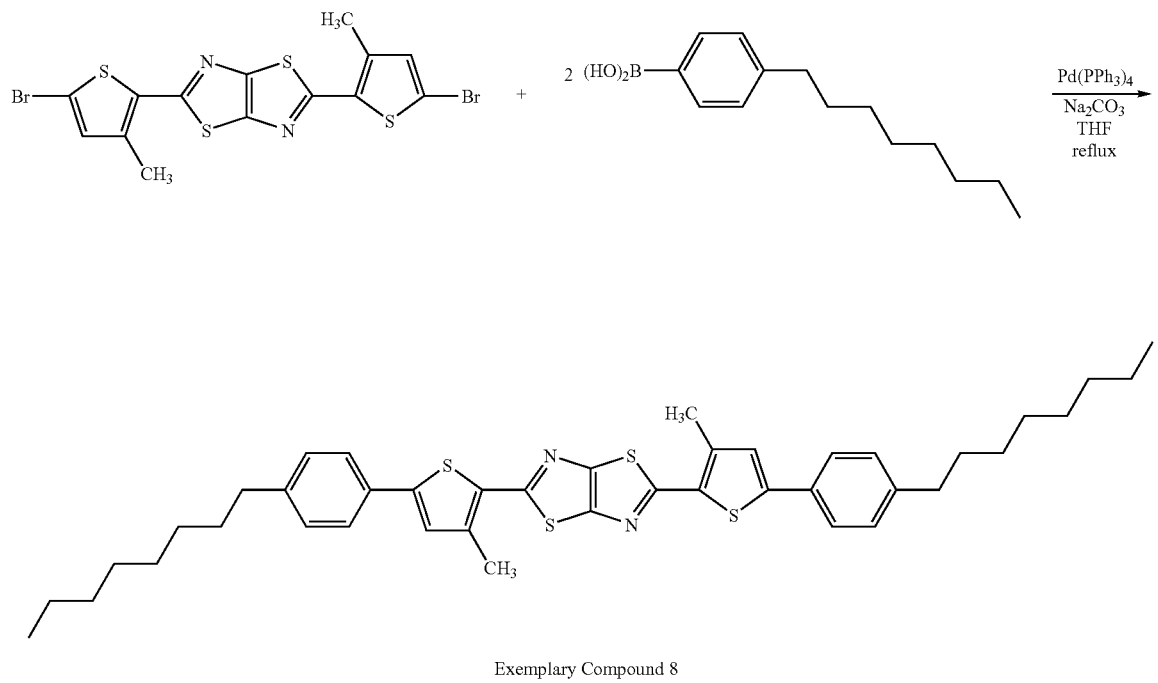

Exemplary Compound 8

Evaluation of Solubility of Thiazolothiazole Derivatives

The solubilities of the thiazolothiazole derivatives obtained in Examples 1 to 10 and the compound represented by Formula 3 as Comparative Example 1 in various solvents are shown in Table 1.

The solubility test is performed as follows:

10 mg (1.0 weight %) of an exemplary compound to be tested is dissolved in 1 ml of a solvent (such as dichlorobenzene, monochlorobenzene, chloroform, THF, toluene or xylene). If the exemplary compound does not dissolve at 25° C., the temperature is increased to the boiling temperature of the solvent. The degree of dissolution is observed with the naked eye.

Evaluation Criteria

A: dissolves even when heating is not conducted

B: completely dissolves when heating is conducted

C: a large proportion thereof dissolves when heating is conducted

D: a small proportion thereof dissolves when heating is conducted

TABLE 1

| | Thiazolothiazole Derivative | Solubility | | | | | |
|---|---|---|---|---|---|---|---|
| | | Dichlorobenzene | Monochlorobenzene | Chloroform | THF | Toluene | Xylene |
| Example 1 | Exemplary Compound (1) | C | C | C | C | C | C |
| Example 2 | Exemplary Compound (11) | C | C | C | C | C | C |
| Example 3 | Exemplary Compound (15) | C | C | C | C | C | C |
| Example 4 | Exemplary Compound (7) | A | A | B | A | B | B |
| Example 5 | Exemplary Compound (4) | B | B | C | C | C | C |
| Example 6 | Exemplary Compound (5) | B | B | C | C | C | C |
| Comparative Example 1 | Compound 3 | D | D | D | D | D | D |
| Example 7 | Exemplary Compound (25) | A | A | A | A | A | A |
| Example 8 | Exemplary Compound (27) | A | A | A | A | A | A |
| Example 9 | Exemplary Compound (28) | A | A | A | A | A | A |
| Example 10 | Exemplary Compound (8) | A | A | B | A | B | B |

It is shown that the thiazolothiazole derivatives synthesized in Examples 1 to 10 have improved solubility, as compared with Compound 3 synthesized in Comparative Example 1. Since the thiazolothiazole derivatives of Examples 1 to 10 have improved solubilities, it is understood that the thiazolothiazole derivatives represented by Formula (I) are highly useful as materials to be used in organic electronic devices such as organic photoreceptors, organic electroluminescence devices, organic transistors, and organic optical memories.

What is claimed is:

1. A thiazolothiazole derivative represented by the following Formula (I):

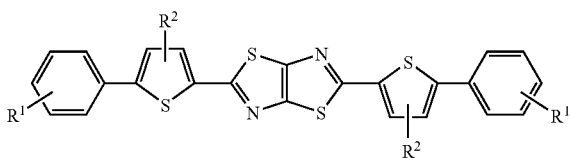

wherein, in Formula (I), each $R^1$ independently represents a $C_3$ to $C_{20}$ straight chain alkyl group, a $C_3$ to $C_{20}$ straight chain alkoxy group, a $C_3$ to $C_{20}$ branched alkyl group, or a $C_3$ to $C_{20}$ branched alkoxy group; and each $R^2$ independently represents a hydrogen atom, a $C_1$ to $C_{20}$ straight chain alkyl group, a $C_1$ to $C_{20}$ straight chain alkoxy group, a $C_3$ to $C_{20}$ branched alkyl group, or a $C_3$ to $C_{20}$ branched alkoxy group.

2. The thiazolothiazole derivative according to claim 1, wherein, in Formula (I), each $R^1$ independently represents a $C_3$ to $C_{12}$ straight chain alkyl group, a $C_3$ to $C_{12}$ straight chain alkoxy group, a $C_3$ to $C_{12}$ main chain portion branched alkyl group or a $C_3$ to $C_{12}$ main chain portion branched alkoxy group, and each $R^2$ independently represents a $C_1$ to $C_{12}$ straight chain alkyl group, a $C_1$ to $C_{12}$ straight chain alkoxy group, a $C_2$ to $C_{12}$ main chain portion branched alkyl group or a $C_2$ to $C_{12}$ main chain portion branched alkoxy group.

3. The thiazolothiazole derivative according to claim 1, wherein, in Formula (I), each $R^1$ independently represents a $C_3$ to $C_{12}$ straight chain alkyl group, a $C_3$ to $C_{12}$ straight chain alkoxy group, a $C_3$ to $C_{12}$ branched alkyl group, or a $C_3$ to $C_{12}$ branched alkoxy group.

4. The thiazolothiazole derivative according to claim 1, wherein, in Formula (I), each $R^2$ independently represents a hydrogen atom, a $C_1$ to $C_8$ straight chain alkyl group, a $C_1$ to $C_8$ straight chain alkoxy group, a $C_3$ to $C_8$ branched alkyl group, or a $C_3$ to $C_8$ branched alkoxy group.

5. The thiazolothiazole derivative according to claim 1, wherein, in Formula (I), each $R^2$ independently represents a $C_1$ to $C_8$ straight chain alkyl group, $C_1$ to $C_8$ straight chain alkoxy group, a $C_3$ to $C_8$ branched alkyl group, or a $C_3$ to $C_8$ branched alkoxy group.

6. The thiazolothiazole derivative according to claim 1, wherein, in Formula (I), each $R^2$ independently represents a $C_3$ to $C_8$ straight chain alkyl group, a $C_3$ to $C_8$ straight chain alkoxy group, a $C_3$ to $C_8$ branched alkyl group having 3 to 8 carbon atoms, or a $C_3$ to $C_8$ branched alkoxy group.

* * * * *